(12) United States Patent
Yamaguchi et al.

(10) Patent No.: US 8,471,220 B2
(45) Date of Patent: Jun. 25, 2013

(54) OPTICAL ANALYSIS DEVICE, OPTICAL ANALYSIS METHOD AND COMPUTER PROGRAM FOR OPTICAL ANALYSIS

(75) Inventors: Mitsushiro Yamaguchi, Hachioji (JP); Seiji Kondo, Hachioji (JP); Tetsuya Tanabe, Tokyo (JP); Kunio Hori, Chofu (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/597,825

(22) Filed: Aug. 29, 2012

(65) Prior Publication Data
US 2013/0048875 A1   Feb. 28, 2013

Related U.S. Application Data

(63) Continuation of application No. PCT/JP2011/053482, filed on Feb. 18, 2011.

(30) Foreign Application Priority Data

Mar. 1, 2010   (JP) .................................. 2010-044714

(51) Int. Cl.
*G01J 1/58* (2006.01)
(52) U.S. Cl.
USPC ...................................... 250/458.1; 250/459.1
(58) Field of Classification Search
USPC ................. 250/203.3, 458.1, 459.1
See application file for complete search history.

(56) References Cited

U.S. PATENT DOCUMENTS

| | | |
|---|---|---|
| 4,251,733 A | 2/1981 | Hirleman, Jr. |
| 6,376,843 B1 | 4/2002 | Palo |
| 6,388,788 B1 | 5/2002 | Harris et al. |
| 6,400,487 B1 | 6/2002 | Harris et al. |
| 6,927,401 B1 | 8/2005 | Palo |
| 8,284,484 B2 | 10/2012 | Hoult et al. |
| 2002/0008211 A1 | 1/2002 | Kask |
| 2002/0036775 A1 | 3/2002 | Wolleschensky et al. |

(Continued)

FOREIGN PATENT DOCUMENTS

| | | |
|---|---|---|
| JP | 04-337446 A | 11/1992 |
| JP | 2002-507762 A | 3/2002 |

(Continued)

OTHER PUBLICATIONS

Kaneshiro, Masataka, "Single Detection Using Fluorescence Correlation Spectroscopy", Protein, Nucleic Acid, Enzyme, 1999, pp. 1431-1438, vol. 44 No. 9.

(Continued)

*Primary Examiner* — Mark R Gaworecki
(74) *Attorney, Agent, or Firm* — Westerman, Hattori, Daniels & Adrian, LLP

(57) ABSTRACT

The inventive optical analysis technique uses an optical system capable of detecting light from a micro region in a solution, such as an optical system of a confocal microscope or a multiphoton microscope, to detect the light from the light-emitting particle to be observed while moving the position of the micro region in the sample solution (while scanning the inside of the sample solution with the micro region); generates time series light intensity data, and after smoothing the time series light intensity data; and detects in the smoothed time series light intensity data the light-emitting particle crossing the inside of the micro region individually, thereby enabling the counting of the light-emitting particle(s) or the acquisition of the information on the concentration or number density of the light-emitting particle.

24 Claims, 10 Drawing Sheets

U.S. PATENT DOCUMENTS

| | | |
|---|---|---|
| 2003/0036855 A1 | 2/2003 | Harris et al. |
| 2003/0218746 A1 | 11/2003 | Sampas |
| 2006/0256338 A1 | 11/2006 | Gartton et al. |
| 2008/0052009 A1 | 2/2008 | Chiu et al. |
| 2010/0033718 A1 | 2/2010 | Tanaami |
| 2010/0177190 A1 | 7/2010 | Chiang et al. |
| 2010/0202043 A1 | 8/2010 | Ujike |

FOREIGN PATENT DOCUMENTS

| | | |
|---|---|---|
| JP | 2002-543414 A | 12/2002 |
| JP | 2004-506192 A | 2/2004 |
| JP | 2005-098876 A | 4/2005 |
| JP | 2007-020565 A | 2/2007 |
| JP | 4023523 B2 | 12/2007 |
| JP | 2008-116440 A | 5/2008 |
| JP | 2008-536093 A | 9/2008 |
| JP | 2008-292371 A | 12/2008 |
| JP | 2009-145242 A | 7/2009 |
| JP | 2009-288161 A | 12/2009 |
| JP | 2011-002415 A | 1/2011 |
| WO | 98/16814 A1 | 4/1998 |
| WO | 99/47963 A | 9/1999 |
| WO | 00/66985 A1 | 11/2000 |
| WO | 02/12864 A1 | 2/2002 |
| WO | 2006/084283 A2 | 8/2006 |
| WO | 2008/007580 A1 | 1/2008 |
| WO | 2008/080417 A1 | 7/2008 |
| WO | 2009/117033 A2 | 9/2009 |

OTHER PUBLICATIONS

Meyer-Almes, F.J., "Nanoparticle Immunoassays: A new Method for Use in Molecular Diagnostics and High Throughput Pharmaceutical Screening based on Fluorescence Correlation Spectroscopy", Fluorescence Correlation Spectroscopy, 2000, pp. 204-224.

Kato, Noriko et al., "A single molecule analyzer that enable new analysis of DNA and protein interactions", Gene & Medicine, 2002, pp. 271-277, vol. 6 No. 2.

International Search Report of PCT/JP2011/053482, mailing date Mar. 29, 2011.

International Preliminary Examination Report, dated Mar. 3, 2012, issued in PCT/JP2011/053482.

Park, Mira et al., "Counting the Number of Fluorophores Labeled in Biomolecules by Observing the Fluorescence-Intensity Transient of a Single Molecule" Bulletin of the Chemical Society of Japan, vol. 78, No. 9, p. 1612-1618, Aug. 30, 2005.

U.S. Office Action mailed Apr. 2, 2013, issued in co-pending U.S. Appl. No. 13/596,280.

FIG. 1A
FIG. 1B
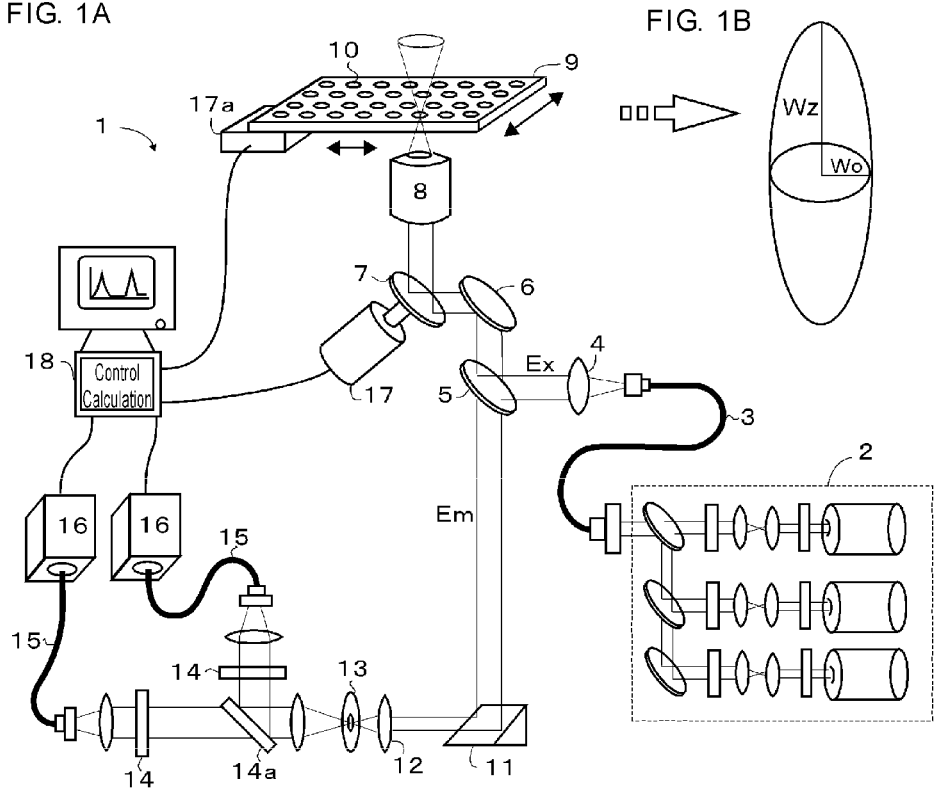
FIG. 1C
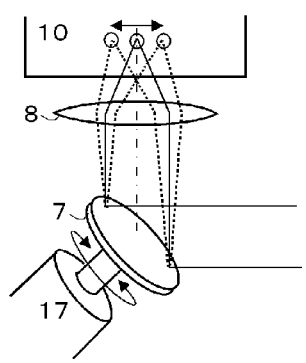
FIG. 1D
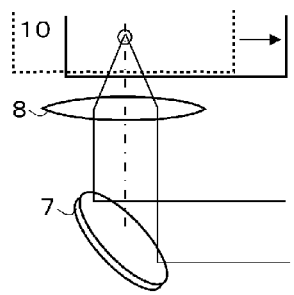

High Concentration (e. g. ~ 1nM)　　FIG. 12A
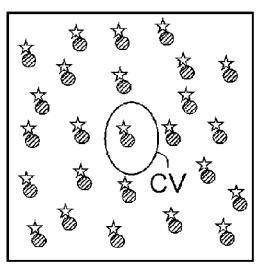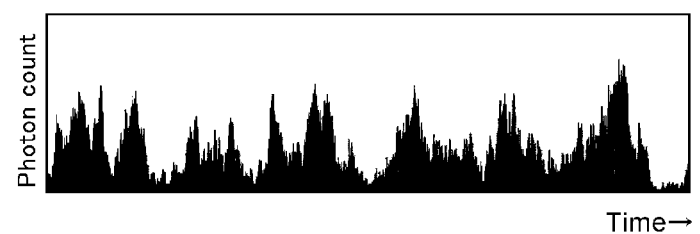
Low Concentration (e. g. ~ 1pM)　　FIG. 12B
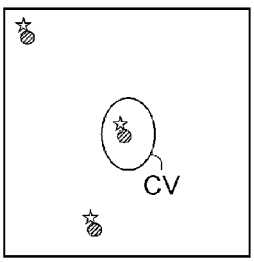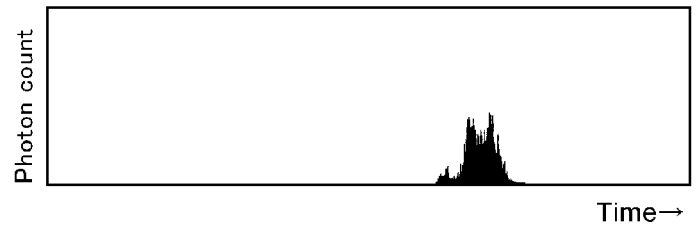

OPTICAL ANALYSIS DEVICE, OPTICAL ANALYSIS METHOD AND COMPUTER PROGRAM FOR OPTICAL ANALYSIS

TECHNICAL FIELD

This invention relates to an optical analysis device, an optical analysis method and a computer program for them, which detects light from an atom, a molecule or an aggregate (Hereafter, these are called a "particle") dispersed or dissolved in a solution, for analyzing the conditions of the particles in the solution, and more specifically, relates to an optical analysis device, an optical analysis method and a computer program for optical analysis, capable of acquiring useful information in an analysis of conditions (interaction, binding or dissociating condition, etc.) of various particles, such as biological molecules, for example, protein, peptide, nucleic acid, lipid, sugar chain, amino acid or these aggregate, particulate objects, e.g. viruses and cells, or non-biological particles by using an optical system, such as the optical system of a confocal microscope or a multiphoton microscope, which can detect light from a micro region in a solution.

BACKGROUND ART

According to the developments in optical measurement techniques in recent years, detection and/or measurement of faint light at a single photon or single fluorescent molecule level have become possible by using an optical system of a confocal microscope and a super high sensitive light detection technique capable of the photon counting (single photon detection). Thus, there are variously proposed devices or methods of performing detection of intermolecular interaction, binding or dissociating reaction of biological molecules, etc. by means of such a faint light measurement technique. For example, in Fluorescence Correlation Spectroscopy (FCS, see e.g. patent documents 1 and 2 and non-patent documents 1-3), by means of the optical system of a laser confocal microscope and a photon counting technique, there is performed the measurement of fluorescence intensity of fluorescence molecules or fluorescently labeled molecules (fluorescent molecules, etc.), entering into and exiting out of a micro region in a sample solution (the focal region to which the laser light of the microscope is condensed, called a "confocal volume"), and based on the average dwell time (translational diffusion time) of the fluorescent molecules, etc. and the average value of the number of the dwelling molecules in the micro region, determined from the autocorrelation function value of the measured fluorescence intensity, there are achieved the acquisition of information, such as the motion speed, the size or the concentration of the fluorescent molecules, etc., and/or the detection of various phenomena, such as a change of a molecular structure or size, a binding or dissociative reaction or dispersion and aggregation of molecules. Further, in Fluorescence Intensity Distribution Analysis (FIDA, e.g. patent document 3) or Photon Counting Histogram (PCH, e.g. patent document 4), there is generated a histogram of fluorescence intensity of fluorescent molecules, etc., entering into and exiting out of a confocal volume, measured similarly to FCS, and the average value of the characteristic brightness of the fluorescent molecules, etc. and the average number of molecules dwelling in the confocal volume are calculated by fitting a statistical model formula to the distribution of the histogram, so that, based on the information thereof, the structure or size change, binding or dissociative conditions or dispersion and aggregation conditions of molecules will be estimated. Moreover, in patent documents 5 and 6, there are proposed methods of detecting fluorescent substances based on a time progress of a fluorescence signal of a sample solution measured using the optical system of a confocal microscope. Patent document 7 has proposed a signal calculation processing technique for measuring faint light from fluorescent fine particles flowing through a flow cytometer or fluorescent fine particles fixed on a substrate by a photon counting technique to detect the existences of the fluorescent fine particles in the flow or on the substrate.

Especially, according to the method employing the fluorescent light measurement technique of a micro region using the optical system of a confocal microscope and a photon counting technique, such as FCS and FIDA, a sample amount required for the measurement may be extremely small (an amount used in one measurement is at most several tens of μL), and its concentration is extremely low as compared with the prior art, and the measuring time is also shortened extremely (In one measurement, measurements for time of order of seconds are repeated several times). Thus, those techniques are expected to be a strong tool enabling an experiment or a test at low cost and/or quickly in comparison with conventional biochemical methods, especially in conducting an analysis of rare or expensive samples often used in the field of the medical or biological research and development or in conducting tests of a large number of specimens, such as sick clinical diagnosis or the screening of bioactive substances.

PRIOR TECHNICAL DOCUMENTS

Patent Documents
Patent document 1: Japanese Patent laid-open publication No. 2005-098876
Patent document 2: Japanese Patent laid-open publication No. 2008-292371
Patent document 3: Japanese Patent No. 4023523
Patent document 4: WO 2008-080417
Patent document 5: Japanese Patent laid-open publication No. 2007-20565
Patent document 6: Japanese Patent laid-open publication No. 2008-116440
Patent document 7: Japanese Patent laid-open publication No. 4-337446
Non-Patent Documents
Non-patent document 1: Masataka Kaneshiro; "Protein, Nucleic acid, Enzyme" Vol. 44, No. 9, pages 1431-1438, 1999.
Non-patent document 2: F. J. Meyer-Alms; "Fluorescence Correlation Spectroscopy" edt. R. Rigler, Springer, Berlin, pages 204-224, 2000.
Non-patent document 3: Noriko Kato, et al. "Gene medicine", Vol. 6, No. 2, pages 271-277.

SUMMARY OF INVENTION

Technical Problem

In the above-mentioned optical analysis techniques, such as FCS, FIDA and PCH, briefly speaking, the magnitude of time fluctuation of measured fluorescence intensity is computed by a statistical procedure, and then various characteristics of fluorescent molecules, etc., entering in and exiting out of a micro region in a sample solution, are determined based on the magnitude of the fluctuation. Thus, in order to obtain a significant result in the above-mentioned optical analysis technique, it is preferable to prepare the concentration or number density of fluorescent molecules, etc. used as the observation objects in the sample solution so that fluorescent molecules, etc. of the number enabling a statistical process will enter in and exit from a micro region in one measuring term of a length of order of seconds in an equilibrium, preferably so that about one fluorescent molecule, etc. will be always exist in the micro region (Typically, since the volume of a confocal volume is about 1 fL, it is preferable that the concentration of fluorescent molecules, etc. is about 1 nM or more). In the other words, when the concentration or number density of particles to be observed in a sample solution is much lower than the level enabling a statistical process (for example, much lower than 1 nM), there would occur a condition where an object to be observed rarely enters into the micro region in the measuring term, and accordingly, the measuring result of fluorescence intensity would include a long period of a condition in which no object to be observed exist at all in the micro region and also the amount of observation of significant fluorescence intensity would decrease, and thus no significant or accurate analysis result could be expected in the optical analysis technique based on the statistical fluctuation of the fluorescence intensity as described above.

In the method of detecting fluorescent substances using the optical system of a confocal microscope described in patent documents 5 and 6, without performing the statistical process of the fluorescence intensity fluctuation as described above, the presence or absence of a fluorescent molecule, etc. to be observed in a sample can be determined from the presence or absence of generation of a fluorescence signal having a significant intensity in the measuring term over several seconds and it is disclosed that a correlation between the frequency of fluorescence signals having significant intensity and the number of the fluorescent molecules, etc. in a sample is obtained. In particular, in patent document 6, it is suggested that the generation of a random flow agitating the inside of a sample solution improves the detection sensitivity. However, even in those methods, the existences of fluorescent molecules, etc. entering into a micro region at random by diffusion or a random flow is simply detected, where the behavior of a particle of the fluorescent molecules, etc. in the micro region cannot be grasped, and therefore, for instance, the counting of particles or the quantitative computing of the concentration or number density of particles have not been achieved. Moreover, the technique described in patent document 7 is to detect individual existences of fluorescent fine particles in the flow in a flow cytometer or fluorescent fine particles fixed on a substrate, not a technique for detecting particles, such as molecules and colloids, being dissolved or dispersed in a normal condition in a sample solution, i.e. particles moving at random in a sample solution, and thus, it has not been achieved to quantitatively compute out the concentration or number density of particles dissolved or dispersed in a sample solution. Further, since the technique of patent document 7 includes processes, such as the measurement in a flow cytometer or the treatment of fixing fluorescence particles on a substrate, the sample amount necessary for the test increases substantially as compared with the cases of the optical analysis techniques, such as FCS, FIDA and PCH, and complicated and advanced operational techniques may be requested to a person conducting the test.

Thus, one of objects of the present invention is to provide a novel optical analysis technique which does not include statistical procedures as performed in optical analysis techniques, such as FCS, FIDA and PCH, so that the detection of a condition or a characteristic of a particle to be observed is enabled in a sample solution containing the particle to be observed at a concentration or number density lower than the level treatable in optical analysis techniques, such as FCS, FIDA and PCH.

In addition, another object of the present invention is to provide an optical analysis device, method or computer program for it, realizing a new optical analysis technique as described above, wherein a measurement can be done with a small sample amount (for example, several tens of μL level) in a short measuring term similarly to optical analysis techniques, such as FCS, FIDA and PCH, and also characteristics, such as a concentration or a number density, of a particle to be observed can be quantitatively determined.

Solution to Problem

Generally, in the present invention, there is proposed a novel type of an optical analysis technique for detecting light from a particle which emits light (hereafter, called a "light-emitting particle"), and is dispersed and moving at random in a sample solution, by means of an optical system which can detect the light from a micro region in a solution, such as an optical system of a confocal microscope or a multiphoton microscope, which technique detects the light from the micro region, i.e., a light detection region, while moving the position of the micro region in the sample solution (i.e., while scanning the inside of the sample solution with the micro region), thereby detecting individually the light-emitting particle crossing the inside of the micro region and enabling the counting of the light-emitting particles and the acquisition of the information on the concentration or number density of the light-emitting particle in the sample solution.

According to the present invention, as one aspect, there is provided an optical analysis device which detects light from a light-emitting particle dispersed and moving at random in a sample solution by using an optical system of a confocal microscope or a multiphoton microscope, characterized in that the device comprises: a light detection region moving mechanism which moves a position of a light detection region of the optical system in the sample solution; a light detector which detects light from the light detection region; and a signal processor which generates time series light intensity data of the light from the light detection region detected with the light detector during moving the position of the light detection region in the sample solution, smoothes the time series light intensity data and then detects individually a light signal from each light-emitting particle in the smoothed time series light intensity data. In this structure, "a light-emitting particle dispersed and moving at random in a sample solution" is a particle, such as an atom, a molecule or an aggregate of these, emitting light and being dispersed or dissolved in a sample solution, and it may be an arbitrary particulate matter making the Brownian motion freely in a solution without being fixed on a substrate, etc. This light-emitting particle is typically a fluorescent particle, but may be a particle which emits light by phosphorescence, chemiluminescence, bioluminescence, light scattering, etc. The "light detection region" of the optical system of a confocal microscope or a multiphoton microscope is the micro region where light is detected in those microscopes, which region corresponds to the region to which illumination light is condensed when the illumination light is given from an objective (This region is determined in accordance with the spatial relationship of an objective and a pinhole especially in a confocal microscope. For a light-emitting particle which emits light without illumination light, for example, a particle which emits light according to chemiluminescence or a bioluminescence, no illumination light is required in a microscope). In this regard, in this specification, "a light signal" means "a signal indicating light".

As understood from the above, in the basic structure of the inventive device, first, the detection of light is sequentially performed while the position of a light detection region is moved in a sample solution, namely, while the inside of the sample solution is scanned with the light detection region. Then, when the moving light detection region includes a randomly moving light-emitting particle, the light from the light-emitting particle is detected by the light detector, and thus, by catching this light, the existence of one light-emitting particle will be detected. In that case, when one light-emitting particle is a single or several fluorescent molecule(s), the light is stochastically emitted from the light-emitting particle, and a gap in the value of the light signal may be generated in minute time. And when such a gap is generated, it will become difficult to specify the signal corresponding to an existence of one light-emitting particle. Thus, the signal processor of the device is designed to sequentially generate time series light intensity data from the signals detected by the light detector and to apply the smoothing treatment to the time series light intensity data, processing the data so that gaps of the light signal value can be ignored, and after that, to detect individually the light signal from each light-emitting particle in the smoothed time series light intensity data. In this regard, typically, the light detector detects the light from the light detection region by the photon counting, and therefore, in that case, the time series light intensity data is time series photon count data.

When a light-emitting particle moving at random in a sample solution becomes individually detectable as described above, various information on conditions of the light-emitting particle within the solution will be acquired. Concretely, for example, in the inventive device, the signal processor may be designed to count the number of the light-emitting particles detected during the moving of the position of the light detection region by counting the number of the individually detected light signals of the light-emitting particles (The Counting of light-emitting particles). According to this structure, by associating the number of light-emitting particles with the moving amount of the position of the light detection region, the information on the number density or concentration of the light-emitting particle in the sample solution will be acquired. Especially, by determining the whole volume of the moving track of the position of the light detection region by an arbitrary method, for example, by moving the position of the light detection region at a predetermined speed, the number density or concentration of the light-emitting particle can be concretely computed. Of course, instead of determining directly the absolute number density value or concentration value, the relative ratio of the number density or concentration to a plurality of sample solutions or a standard sample solution to be a reference of a concentration or a number density may be computed.

In the processes of the signal processor of the inventive device, the judgment of whether or not one light-emitting particle has entered in the light detection region may be done based upon a shape of a light signal in the smoothed time series light intensity data. In an embodiment, typically, when a light signal having the intensity larger than a predetermined threshold value is detected, it may be detected that one light-emitting particle has entered into the light detection region.

Moreover, in the above-mentioned inventive device, the moving speed of the position of the light detection region in the sample solution is appropriately changed based on the characteristic of the light-emitting particle or the number density or concentration of the light-emitting particle in the sample solution. As understood by ones ordinarily skilled in the art, the condition of detected light from the light-emitting particle may change in accordance with the characteristic of the light-emitting particle or the number density or concentration of a light-emitting particle in a sample solution. Especially, when the moving speed of the light detection region becomes quick, the amount of light obtained from one light-emitting particle will be reduced, and therefore it is preferable that the moving speed of the light detection region can be changed appropriately so that the light from one light-emitting particle can be measured with precisely or sufficient sensitivity.

Furthermore, in the inventive device, the moving speed of the position of the light detection region in the sample solution is preferably set to be higher than the diffusional moving velocity of a light-emitting particle to be a detected object (the average moving speed of a particle owing to the Brownian motion). As explained above, the inventive device detects light emitted from a light-emitting particle when the light detection region passes through the position where the light-emitting particle exists, thereby detecting the light-emitting particle individually. However, when the light-emitting particle moves at random owing to the Brownian motion to move into and out of the light detection region multiple times, the light signal from one light-emitting particle (showing the existence of the light-emitting particle) will be detected multiple times, and therefore it would becomes difficult to make the existence of one light-emitting particle associated with the detected light signal. Then, as described above, the moving speed of the light detection region is set higher than the diffusional moving velocity of the light-emitting particle, and thereby it becomes possible to make one light-emitting particle correspond to one light signal (indicating the existence of a light-emitting particle). In this regard, since the diffusional moving velocity differs depending upon a light-emitting particle, preferably, the inventive device may be designed to be capable of changing the moving speed of the light detection region appropriately according to the characteristics (especially, the diffusion constant) of the light-emitting particle as described above.

The changing of the optical path of the optical system for moving the position of the light detection region may be done in an arbitrary way. For example, the position of the light detection region may be changed by changing the optical path using a galvanomirror employed in the laser scan type light microscope, or while the light detection region is immobilized, the position of the light detection region in the sample solution may be moved by moving the position of the sample solution (moving the stage of a microscope). The movement track of the position of the light detection region may be set arbitrarily, for example, which is selectable from circular, elliptical, rectangular, straight and curvilinear ones.

In an embodiment, the inventive optical analysis device which detects light from a light-emitting particle in a sample solution using an optical system of a confocal microscope or a multiphoton microscope, may be designed to detect individually a light signal from each light-emitting particle entering into the inside of a light detection region while moving the light detection region of the optical system in the sample solution at a velocity faster than the diffusional moving velocity of the light-emitting particle within the sample solution and to detect the number of the light-emitting particles entering into the light detection region by counting the light signals.

The processes of the optical analysis technique of performing light detection together with moving the position of the light detection region in a sample solution, and detecting individually the light signal from each light-emitting particle in the above-mentioned inventive device is realizable also by a general purpose computer. Therefore, according to another aspect of this invention, there is provided a computer readable storage device having a computer program product including programmed instructions for optical analysis for detecting light from a light-emitting particle dispersed and moving at random in a sample solution by using an optical system of a confocal microscope or a multiphoton microscope, said programmed instructions causing a computer to perform steps of: moving a position of a light detection region of the optical system in the sample solution; detecting light from the light detection region during moving the position of the light detection region in the sample solution to generate time series light intensity data; smoothing the time series light intensity data; and detecting individually a light signal from each light-emitting particle in the smoothed time series light intensity data.

Also, this computer program may comprise the step of counting the number of the light-emitting particles detected during moving the position of the light detection region by counting the number of the individually detected light signals from the light-emitting particle and/or the step of determining the number density or concentration of the light-emitting particle in the sample solution based on the number of the detected light-emitting particles. Typically, in the step of detecting the light from the light detection region to generates time series light intensity data, the light from the light detection region is detected by photon counting, and in that case, the time series light intensity data is time series photon count data. In the step of moving the position of the light detection region, the position of the light detection region may be moved at a predetermined velocity or a velocity faster than a diffusional moving velocity of the light-emitting particle, and the moving speed of the position of the light detection region may be set based on a characteristic of the light-emitting particle or the number density or concentration of the light-emitting particle in the sample solution. Furthermore, in the signal processing, the entering of one light-emitting particle into the light detection region may be judged based on the shape of a light signal in the smoothed time series light intensity data, for instance, at the detection of the light signal which has the intensity larger than a predetermined threshold value. The movement track of the position of the light detection region may be selected from circular, elliptical, rectangular, straight and curvilinear ones.

Furthermore, according to the above-mentioned inventive device or computer program, there is realized a novel optical analysis method of detecting individually a light signal from each light-emitting particle through detecting light together with moving the position of the light detection region in a sample solution. Thus, the inventive optical analysis method of detecting light from a light-emitting particle dispersed and moving at random in a sample solution by using an optical system of a confocal microscope or a multiphoton microscope is characterized by comprising steps of: moving a position of a light detection region of the optical system in the sample solution; detecting light from the light detection region during moving the position of the light detection region in the sample solution to generate time series light intensity data; smoothing the time series light intensity data; and detecting individually a light signal from each light-emitting particle in the smoothed time series light intensity data.

This method may also comprise the step of counting the number of the light-emitting particles detected during moving the position of the light detection region by counting the number of the individually detected light signals from the light-emitting particle and/or the step of determining the number density or concentration of the light-emitting particle in the sample solution based on the number of the detected light-emitting particles. Further, in the step of moving the position of the light detection region, the position of the light detection region may be moved at a predetermined velocity or a velocity faster than a diffusional moving velocity of the light-emitting particle, and the moving speed of the position of the light detection region may be set based on a characteristic of the light-emitting particle or the number density or concentration of the light-emitting particle in the sample solution. Furthermore, in the signal processing step, the entering of one light-emitting particle into the light detection region may be judged based on the shape of a light signal in the smoothed time series light intensity data, for instance, at the detection of the light signal which has the intensity larger than a predetermined threshold value.

Effects of Invention

The optical analysis technique realized by the above-mentioned inventive device, method or computer program employs, for its light detecting mechanism itself, a structure to detect light from a light detection region in a confocal microscope or a multiphoton microscope similarly to the cases of optical analysis techniques, such as FCS, FIDA and PCH, and thus the amount of a sample solution may be similarly small. However, since no statistical procedure of computing the fluorescence intensity fluctuation is performed in the present invention, the inventive optical analysis technique is applicable to a sample solution in which the number density or concentration of a light-emitting particle is substantially lower than the level required for the optical analysis techniques, such as FCS, FIDA and PCH.

Moreover, since each light-emitting particle dispersed or dissolved in a solution is individually detected in this invention, it becomes quantitatively possible by using the information thereon to conduct the counting of light-emitting particles, the computation of the concentration or number density of the light-emitting particle in a sample solution or the acquisition of the information on the concentration or number density. For example, although patent documents 5 and 6 could acquire the correlation between the aggregate in the frequency of fluorescence signals having an intensity beyond a predetermined threshold value within a predetermined time and the number of particles of fluorescent molecules, etc. in a sample solution, it is impossible to grasp the dynamic behavior of a particle passing through the measuring region (whether a particle passes straight through the measuring region or dwells within the measuring region), and therefore the correspondence between a fluorescence signal having an intensity higher than a predetermined threshold value and a particle passing through the measuring region is not clear, so that the counting of light-emitting particles was theoretically impossible and it was difficult to determine precisely the concentration of particles in a sample solution. However, since, according to this invention, a light-emitting particle passing through a light detection region is made associated with a detected light signal in 1 to 1 manner so that one light-emitting particle will be detected at one time, the counting of light-emitting particles dispersed and moving at random in a solution becomes possible, and it becomes possible to determine the concentration or number density of the particle in a sample solution precisely as compared with the conventional art.

The inventive optical analysis technique is typically used for analyses of conditions in a solution of biological particulate objects, such as biological molecules, e.g., a protein, a peptide, a nucleic acid, a lipid, a sugar chain, an amino acid or an aggregate of these, a virus and a cell, although it may be used for analyses of conditions of non-biological particles in a solution (for example, an atom, a molecule, a micelle, a metallic colloid, etc.), and it should be understood that such cases are included in the scope of the present invention, also. In this respect, in the present invention, according to the manner that, after smoothing the time series light intensity data of the light from the light detection region detected in the light detector, a light signal from each light-emitting particle is detected individually in the smoothed time series light intensity data, even in a case that a gap in a minute time may arise in the value of the light signal from one light-emitting particle because the light is stochastically emitted from one light-emitting particle and the number of the particles is small, such as when a light-emitting particle is a single fluorescent molecule, the making of the correspondence between a light signal appearing on the light intensity data and a light-emitting particle will be precisely possible, and therefore, the more precise counting of the number of light-emitting particles, and in turn, the measurement of the concentration or number density of the light-emitting particle in good conditions becomes possible. [In the cases of patent documents 5 and 6, a light signal appearing on time series light intensity data is not associated with a light-emitting particle. Also, in the case of the technique for detection of light-emitting particles with the fluorescence measurement in the conventional flow cytometry, since the observed light-emitting particles are particles carrying many fluorescence molecules, no substantial gap in a minute time is generated in the value of a light signal from a single light-emitting particle of one light-emitting particle, and thus the smoothing of light intensity data is not conducted.]

Other purposes and advantages of the present inventions will become clear by explanations of the following preferable embodiments of the present invention.

BRIEF DESCRIPTIONS OF DRAWINGS

FIG. 1A is a schematic diagram of the internal structure of the optical analysis device according to the present invention. FIG. 1B is a schematic diagram of a confocal volume (an observation region of a confocal microscope). FIG. 1C is a schematic diagram of the mechanism for changing the direction of the mirror 7 to move the position of a light detection region in a sample solution. FIG. 1D is a schematic diagram of the mechanism for moving the horizontal position of a micro plate to move the position of a light detection region in a sample solution.

Figure 4A:
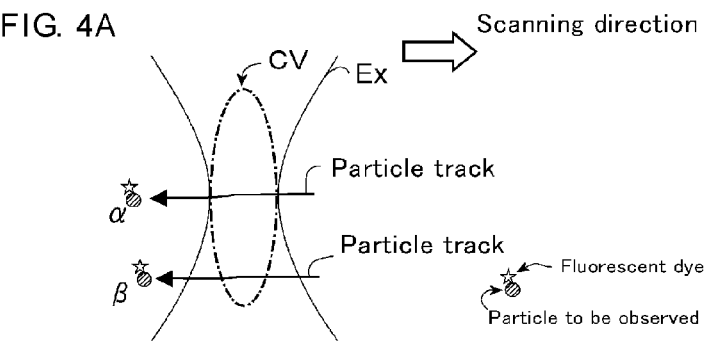
Figure 4B:
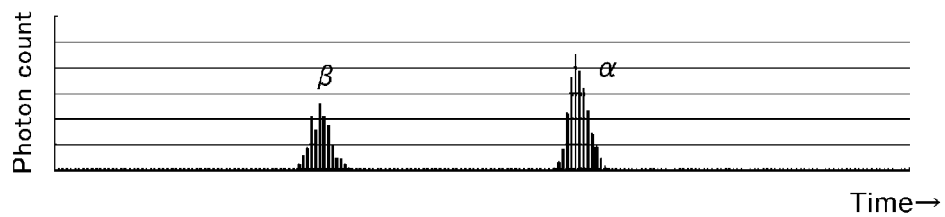

FIGS. 4A and 4B are a drawing of a model in the case that a light-emitting particle crosses a light detection region by moving the position of the light detection region in a sample solution at a velocity faster than the diffusional moving velocity of the light-emitting particle, and a diagram showing the example of the variation of the photon counts (light intensity) with time in this case, respectively.

FIG. 5 are drawings explaining one example of a signal processing step for conducting the counting of light-emitting particles from the time variation of photon counts (light intensity) measured by the inventive optical analysis technique, including a binarization process of the detected signals.

Figure 6A:
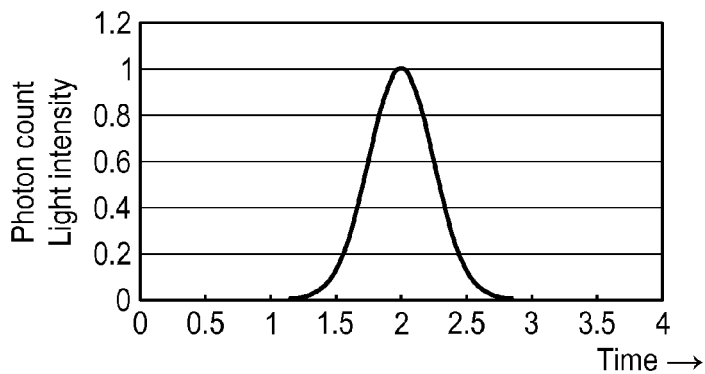

FIG. 6 is are drawings explaining one example of a signal processing step for conducting the counting of light-emitting particles from the time variation of the photon counts (light intensity) measured by the inventive optical analysis technique, including the differentiation processing of the detected signals.

Figure 7:
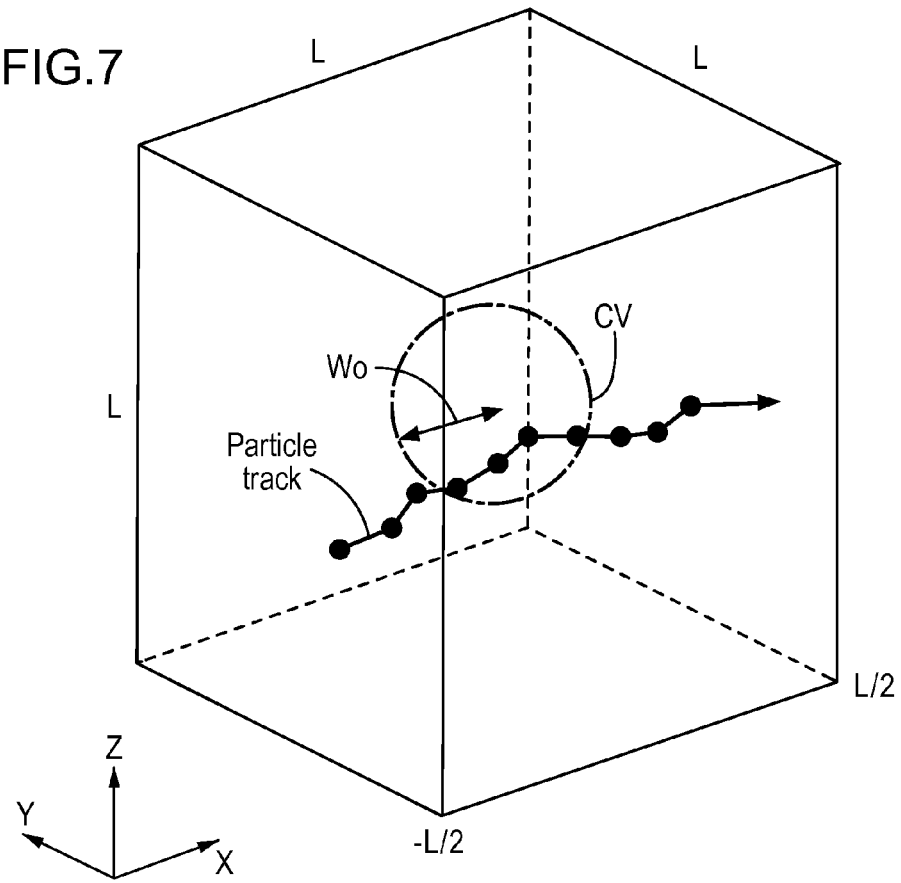

FIG. 7 is a diagram explaining a model for a calculation experiment of detection and counting of light-emitting particles by the inventive optical analysis technique.

Figure 8A:
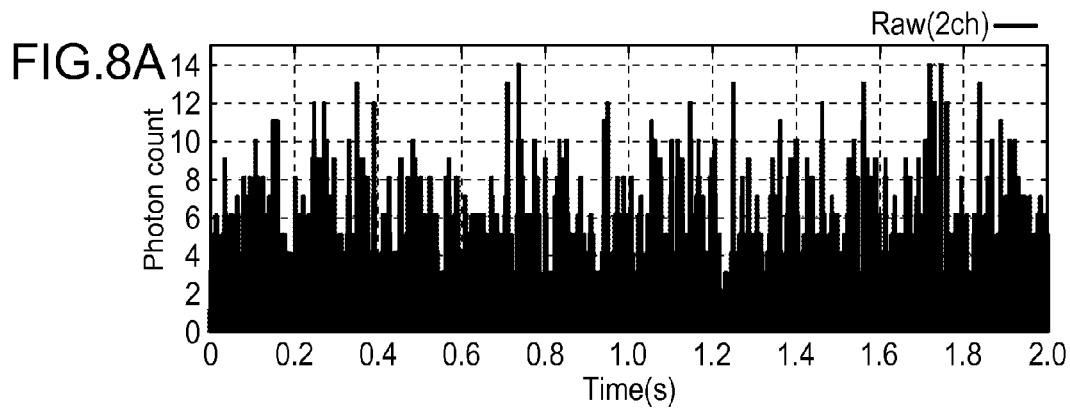
Figure 8B:
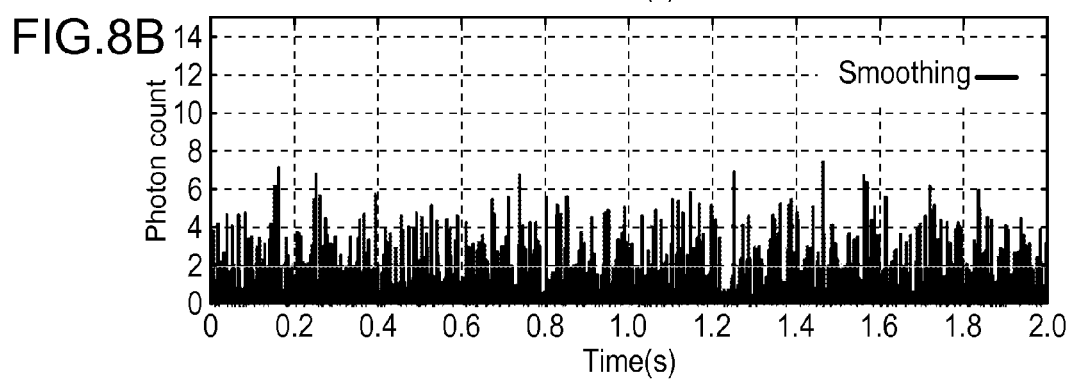
Figure 8C:
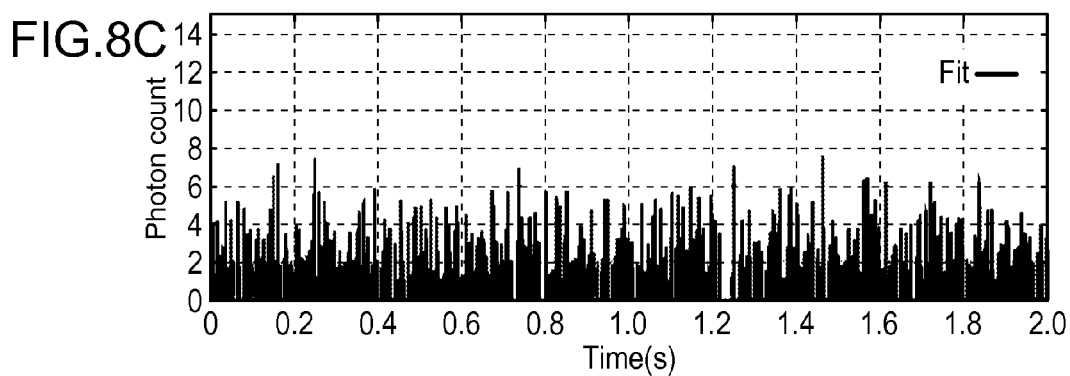
Figure 8D:
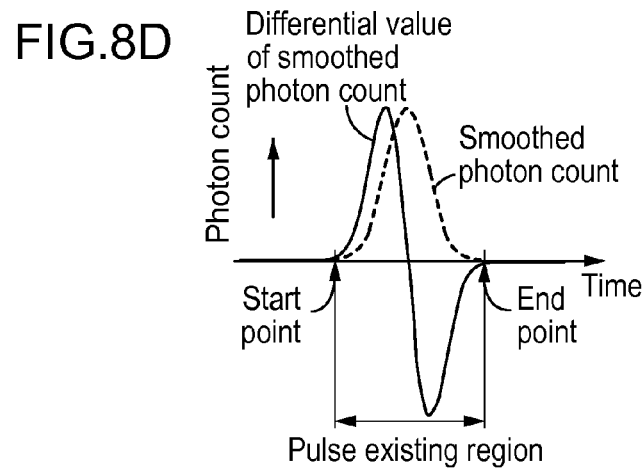

FIGS. 8A, 8B and 8C each show examples of time series photon count data measured by the inventive optical analysis technique; smoothed time series photon count data (data acquired by applying smoothing treatment to time series photon count data); and gauss function curves fitted on the smoothed time series photon count data. FIG. 8D shows the process for determining a pulse existing region in the smoothed time series photon count data.

Figure 9:
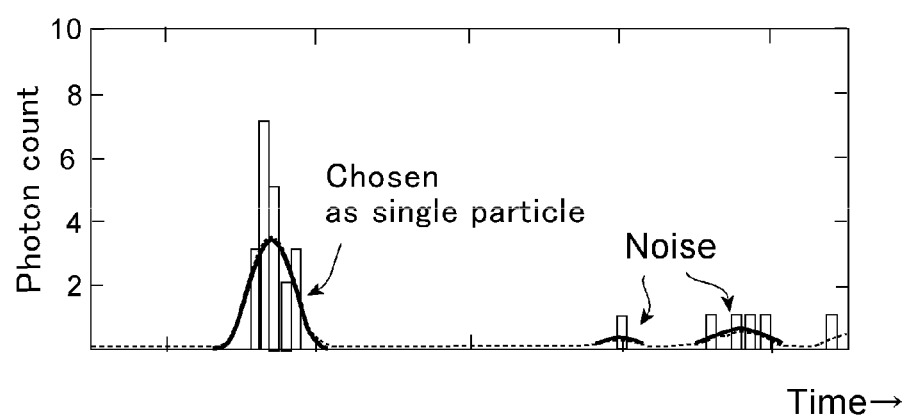

FIG. 9 shows examples of photon count data measured by the inventive optical analysis technique (bar graph); curve obtained by carrying out the smoothing of the data (dotted line); and gauss functions fitted on the peak existing region (solid line). In the drawing, the signals attached with "noise" are disregarded as signals due to noises or contaminants.

Figure 10A:
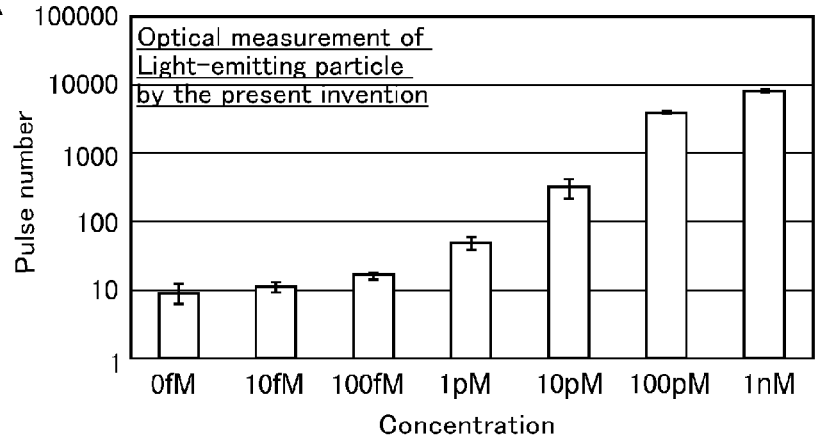
Figure 10B:
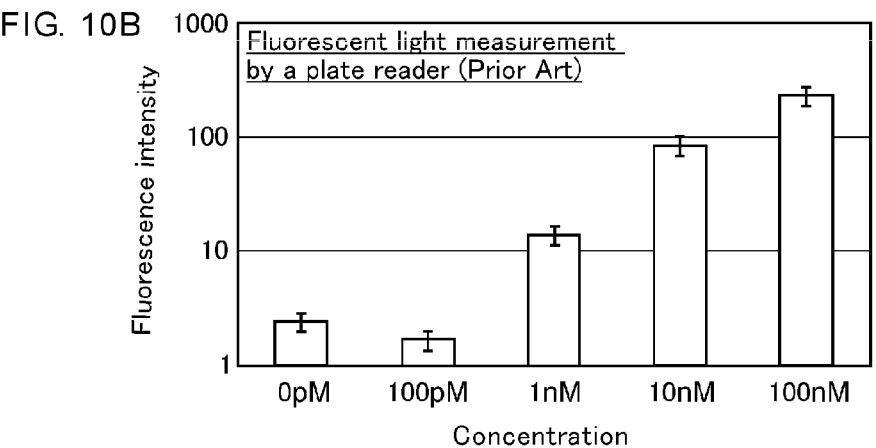
Figure 10C:
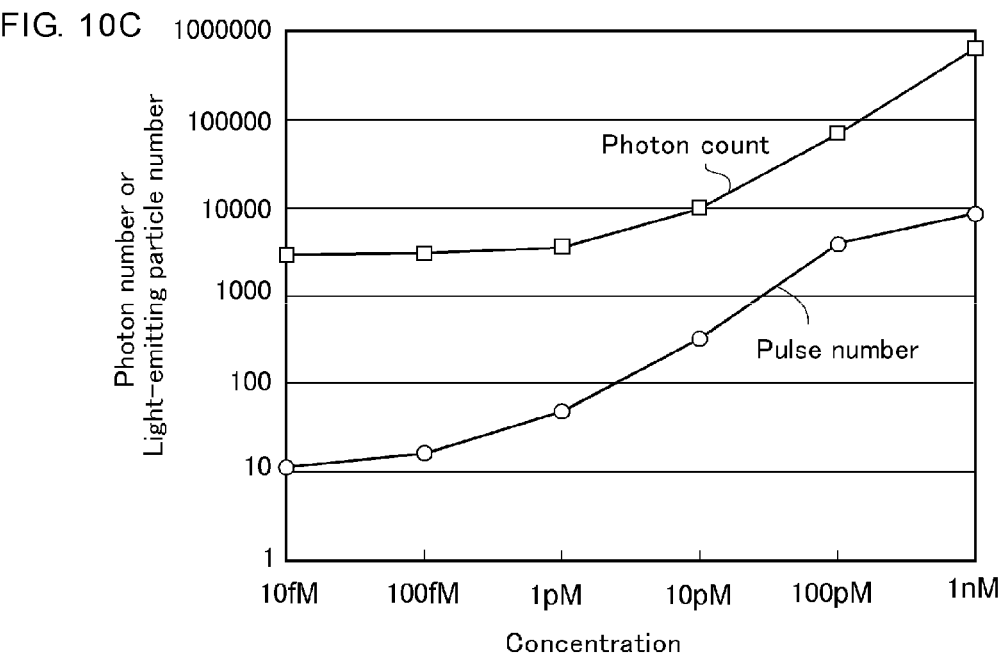

FIGS. 10A and 10B show a result of the light emitting particle count detection experiment according to the present invention and a result of a fluorescence intensity measurement experiment of light-emitting particles using a plate reader, respectively. In the drawings, the vertical graphs each indicate the averages value of three times of measurements, and the error bars show the SD values of three times of measurements. FIG. 10C is a graph by plotting the numbers of the pulse signals corresponding to the light-emitting particle detected in the time series photon count data obtained by performing the light emitting particle count detection experiment in accordance with the present invention (pulse number) and the totals of the photon numbers detected in the same time series photon count data (photon number) against the light-emitting particle concentrations in the respective sample solutions.

Figure 11A:
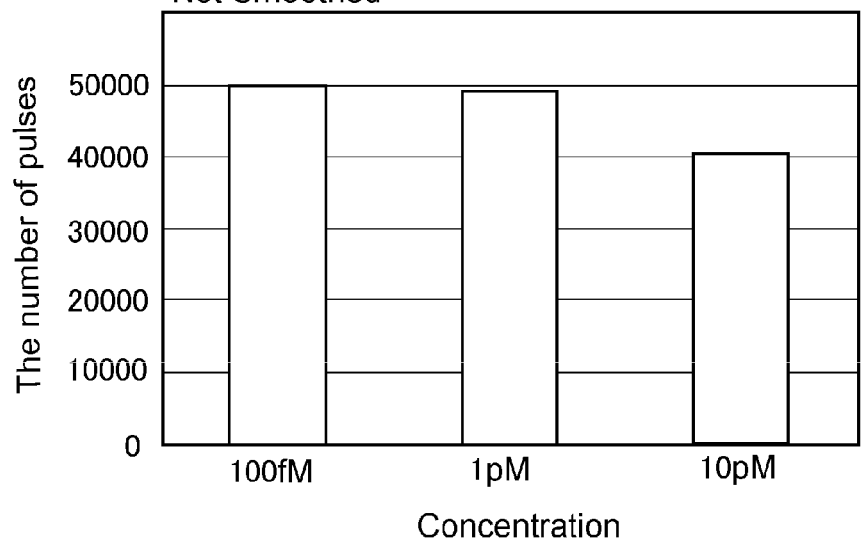
Figure 11B:
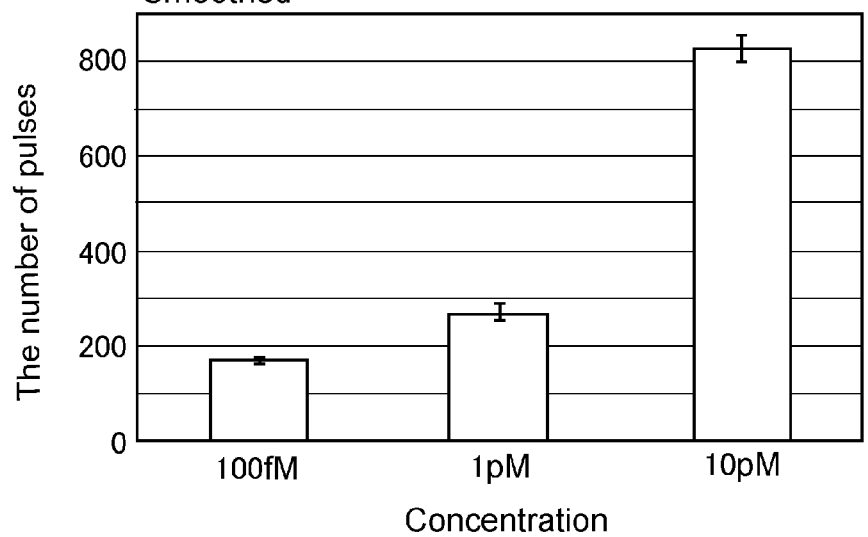

FIG. 11A is a drawing showing in a graph form the number of signals detected as a pulse signal corresponding to a light-emitting particle in the time series photon count data, to which no smoothing treatment is applied, with respect to sample solutions containing light-emitting particles at 100 fM, 1 pM, and 10 pM, and FIG. 11B is a drawing showing in a graph form the number of the signals detected as a pulse signal corresponding to a light-emitting particle in the time series photon count data, to which the smoothing treatment has been applied, with respect to the same sample solutions.

FIG. 12 shows examples of the time variation of the photon count (light intensity) obtained in a conventional optical analysis technique computing fluorescence intensity fluctuation, where 12A shows a case that the particle concentration is at a level providing a sufficient precision in the measurement, and 12B shows a case that the particle concentration in a sample is significantly lower than the case of 12A.

EXPLANATIONS OF REFERENCE NUMERALS

1 - - - Optical analysis device (confocal microscope)
2 - - - Light source
3 - - - Single mode optical fiber
4 - - - Collimating lens
5 - - - Dichroic mirror
6, 7, 11 - - - Reflective mirror
8 - - - Objective
9 - - - Micro plate
10 - - - Well (sample solution container)
12 - - - Condenser lens
13 - - - Pinhole
14 - - - Barrier filter
15 - - - Multi-mode optical fiber
16 - - - Photodetector
17 - - - Mirror deflector
17a - - - Stage position changing apparatus
18 - - - Computer

DESCRIPTION OF EMBODIMENTS

In the followings, preferable embodiments of the present invention are described in detail.

The Structure of an Optical Analysis Device

The basic structure of the optical analysis device which realizes the inventive optical analysis technique may be a device formed by combining an optical system of a confocal microscope and a photodetector as schematically illustrated in FIG. 1A, with which FCS, FIDA, etc. can be performed. Referring to the drawing, the optical analysis device 1 consists of an optical system 2-17 and a computer 18 for acquiring and analyzing data together with controlling the operation of each part in the optical system. The optical system of the optical analysis device 1 may be the same as the optical system of a usual confocal microscope, where laser light emitted from a light source 2 and transmitted through the inside of a single mode fiber 3 (Ex) forms light diverging to be radiated at the angle decided by an inherent NA at the emitting end of the fiber; and after forming a parallel beam with a collimator 4, the light is reflected on a dichroic mirror 5 and reflective mirrors 6 and 7, entering into an objective 8. Above the objective 8, typically, there is placed a sample container or a micro plate 9 having wells 10 arranged thereon, to which one to several tens of μL of a sample solution is dispensed, and the laser light emitted from the objective 8 is focused in the sample solution in the sample container or well 10, forming a region having strong light intensity (excitation region). In the sample solution, light-emitting particles to be observed objects, which are fluorescent particles or particles to which a light emitting label such as a fluorescent dye is attached, are dispersed or dissolved, and when a light-emitting particle enters into the excitation region, the light-emitting particle during dwelling in the excitation region is excited, emitting light. The emitted light (Em), after passing through the objective 8 and the dichroic mirror 5, is reflected on the mirror 11 and condensed by a condenser lens 12, and then the light passes through the pinhole 13; transmits through a barrier filter 14 (where light components only in a specific wavelength band region are selected); and is introduced into a multimode fiber 15, reaching to a photodetector 16, and after the conversion into time series electric signals, the signals are inputted into the computer 18, where the processes for optical analyses are executed in manners explained later. In this regard, as known in ones skilled in the art, in the above-mentioned structure, the pinhole 13 is located at a conjugate position of the focal position of the objective 8, and thereby only the light emitted from the focal region of the laser light, i.e., the excitation region, as schematically shown in FIG. 1B, passes through the pinhole 13 while the light from regions other than the excitation region is blocked. The focal region of the laser light illustrated in FIG. 1B is a light detection region in this light analysis device, whose effective volume is usually about 1-10 fl, (Typically, the light intensity is spread in accordance with a Gaussian distribution having the peak at the center of the region. The effective volume is a volume of an approximate ellipsoid bordering a surface where the light intensity reduced to $1/e^2$ of the peak intensity), which is called as "confocal volume". Moreover, since the light from one light-emitting particle, for example, the faint light from one fluorescent dye molecule, is detected in this invention, preferably, a super high sensitive photodetector, usable for the photon counting, is used for the photodetector 16. When the detection of light is performed by the photon counting, the measurement of light intensity is sequentially performed in the manner of measuring the number of photons arriving at the photodetector for every predetermined unit time (BIN TIME) in a predetermined term. Thus, in this case, the time series light intensity data is time series photon count data. Further, on the stage (not shown) of the microscope, there may be provided a stage position changing apparatus 17a for moving the horizontal position of the micro plate 9, in order to change the well 10 to be observed. The operation of the stage position changing apparatus 17a may be controlled by the computer 18. According to this structure, quick measurement can be achieved even in the presences of two or more specimens.

Furthermore, in the optical system of the above-mentioned optical analysis device, there is provided a mechanism for scanning the inside of the sample solution with the light detection region, i.e., the focal region, namely for moving the position of the light detection region within the sample solution. For this mechanism for moving the position of the light detection region, for example, as schematically illustrated in FIG. 1C, there may be employed a mirror deflector 17 which changes the direction of the reflective mirror 7 (Type of moving the absolute position of the light detection region). This mirror deflector 17 may be the same as that of a galvanomirror device equipped on a usual laser scan type microscope. Or, alternatively, as illustrated in FIG. 1D, the stage position changing apparatus 17a may be operated to move the horizontal position of the container 10 (micro plate 9) into which a sample solution has been dispensed for moving the relative position of the light detection region in the sample solution (Type of moving the absolute position of a sample solution). Even in either of the types, in order to attain a desired moving pattern of the position of the light detection region, the mirror deflector 17 or the stage position changing apparatus 17a is driven in harmony with the light detection of the photodetector 16 under the control of the computer 18. The movement track of the position of the light detection region may be arbitrarily selected from circular, elliptical, rectangular, straight and curvilinear ones, or a combination of these (In the program in the computer 18, it may be designed so that various moving patterns can be selected). In this regard, although not illustrated, the position of the light detection region may be moved in the vertical direction by moving the objective 8 up and down.

In the case that the light-emitting particle used as an object to be observed emits light by multiple photon absorption, the above-mentioned optical system is used as a multiphoton microscope. In that case, since the light is emitted only from the focal region of the excitation light (light detection region), the pinhole 13 may be removed. Further, in the case that the light-emitting particle used as an object to be observed emits light owing to a chemiluminescence or bioluminescence phenomenon without excitation light, the optical system 2-5 for generating excitation light may be omitted. When the light-emitting particle emits light owing to phosphorescence or scattered light, the above-mentioned optical system of the confocal microscope is used as it is. Furthermore, in the optical analysis device 1, as shown in the drawing, two or more excitation light sources 2 may be provided so that the wave length of the excitation light can be selected appropriately in accordance with the excitation wave length of the light-emitting particle. Similarly, two or more photodetectors 16 may also be provided so that, when the sample contains two or more kinds of light-emitting particles whose wave lengths differ from one another, the respective lights from them can be detected separately in accordance with the wave lengths.

The Principle of the Inventive Optical Analysis Technique

Spectral analysis techniques, such as FCS and FIDA, are advantageous in that the required sample amount is extremely small and a test can be performed promptly as compared with the conventional biochemical analytical techniques. However, in these spectral analysis techniques such as FCS and FIDA, the concentration and characteristics of a particle to be observed are principally computed based on the fluorescence intensity fluctuation, and therefore, in order to obtain accurate measurement results, the concentration or number density of the particle to be observed in a sample solution should be at a level where about one particle to be observed always exists in a light detection region CV during the fluorescence intensity measurement as schematically drawn in FIG. 11A so that significant light intensity (photon count) can be always detected in the measuring term as shown in the right-hand side of the drawing. When the concentration or number density of the particle to be observed is lower than that, for example, at the level where the particle to be observed rarely enters into the light detection region CV as drawn on FIG. 11B, no significant light intensity (photon count) would appear in a part of the measuring term as illustrated on the right-hand side of the drawing, and thus, accurate computation of light intensity fluctuation would become difficult. Also, when the concentration of the particle to be observed is significantly lower than the level where about one particle to be observed always exists in the inside of the light detection region during the measurement, the calculation of light intensity fluctuation would become subject to the influence of the background, and the measuring term should be made long in order to obtain the significant quantity of the light intensity data (photon count), sufficient for the calculation.

Then, in the present invention, there is proposed an optical analysis technique based on a new principle enabling the detection of characteristics, such as the number density or concentration of a particle to be observed, even when the concentration of the particle to be observed is lower than the level requested in the above-mentioned spectral analysis techniques, such as FCS and FIDA.

Figure 2A:
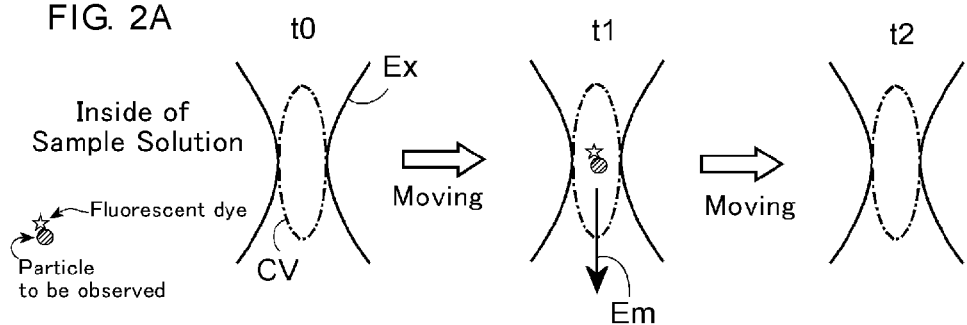
FIGS. 2A and 2B are a schematic diagram explaining the principle of the light detection by the optical analysis technique according to the present invention and a schematic diagram of the variation of the measured light intensity with time, respectively.
Figure 2B:
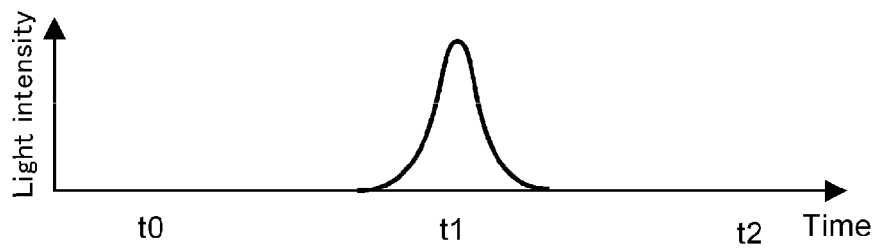

In the inventive optical analysis technique, briefly speaking, as the processes to be performed, the light detection is performed together with moving the position of the light detection region CV in a sample solution, namely, scanning the inside of the sample solution with the light detection region CV by driving the mechanism (mirror deflector 17 or stage position changing apparatus 17a) for moving the position of the light detection region as schematically drawn in FIG. 2. Then, for example, as in FIG. 2A, during the moving of the light detection region CV (in the drawing, time t0-t2), when the light detection region CV passes through a region where one light-emitting particle (In the drawing, a fluorescent dye) exists (t1), a significant light intensity (Em) will be detected as a pulse form signal, as drawn in FIG. 2B. Thus, by detecting, one by one, each significant light intensity, i.e. each pulse form signal, appearing as illustrated in FIG. 2B during the execution of the moving of the position of the light detection region CV and the light detection as described above, the light-emitting particles are detected individually, and by counting the number thereof, the information about the number, concentration or number density of the light-emitting particles existing in the measured region can be acquired. It should be understood that, in the principle of this inventive optical analysis technique, no statistical calculation processes, such as the calculation of the fluorescence intensity fluctuation, are conducted and the light-emitting particles are one by one detected, and therefore, the information about the concentration or number density of the light-emitting particle is acquirable even in a sample solution with a low concentration of the light-emitting particle (particle to be observed) at the level where no sufficiently precise analysis is available in FCS and FIDA.

Figure 2C:
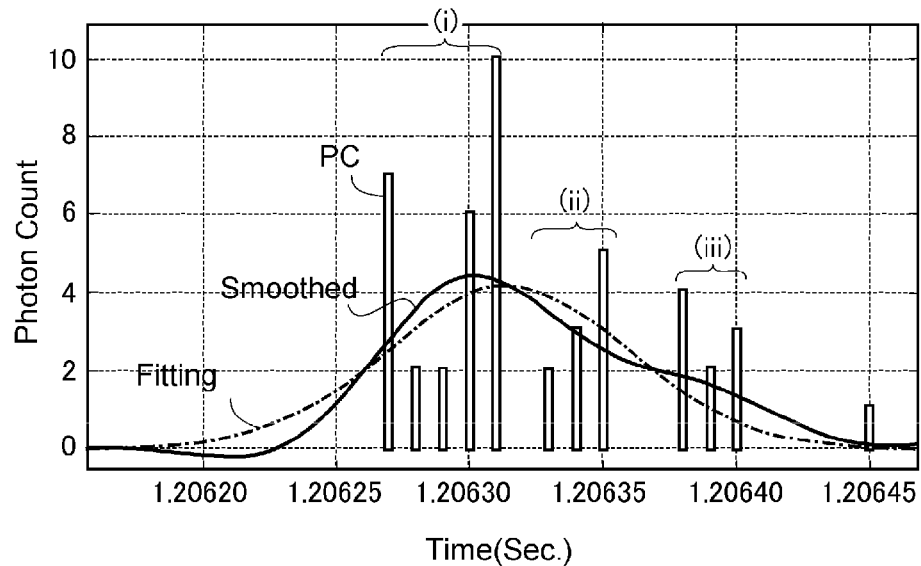
FIG. 2C is a schematic diagram of a photon count data in performing a smoothing treatment and a fitting process.

In this regard, as already noted in the column of "Summary of invention", in a case that a light-emitting particle is a fluorescent dye, etc. at the single or several molecular level, the number of photons emitted from the light-emitting particle is small and the photon is emitted stochastically. Thus, in the actual light intensity data (photon count data), the value (PC) of the photon count (light intensity) may have a gap in minute time as illustrated in FIG. 2C, and thereby, if it is tried to detect the light signal of a light-emitting particle from the raw photon count data, the light from one light-emitting particle may happen to be erroneously detected as the lights from two or more light-emitting particles. For instance, in the illustrated example, although the group of photon counts PC is considered as the light from one light-emitting particle, due to the presences of the gaps in minute time, for example, it is possible to misidentify three signal groups (i), (ii), and (iii) as signals corresponding to different light-emitting particles. Thus, in the present invention, the smoothing treatment is applied to the raw photon count data using a moving average method, etc. When the smoothing treatment is applied, as drawn with solid line in the drawing, the photon count value changes to an approximately bell-shaped pulse signal, and thereby the detection of a signal corresponding to the light from one light-emitting particle becomes easy so that the possibility of misidentifying a light signal from one light-emitting particle as light signals from two or more light-emitting particles will be reduced. Furthermore, the detection of a signal corresponding to the light from a light-emitting particle in the smoothed photon count data may be achieved by fitting a bell type functions, such as Gaussian function as drawn with alternate long and short dash line in the drawing, to each pulse form signal appearing in the smoothed photon count data, and judging whether or not each pulse form signal is a signal corresponding to the light from a light-emitting particle based on the result of the fitting.

Operations of the Inventive Light Analysis Device and Operation Processes

Concretely, in the optical analysis with the inventive optical analysis device 1 as illustrated in FIG. 1A, there are conducted (1) a process of measuring the light intensity of a sample solution containing light-emitting particles (particles to be observed) and (2) a process of analyzing the measured light intensity.

(1) Measurement of the Light Intensity of a Sample Solution

The particle used as the object to be observed in the inventive optical analysis technique may be an arbitrary particle as long as it is dispersed and moving at random in a sample solution, such as a dissolved molecule, and the particle may be, for instance, a biological molecule, i.e. a protein, a peptide, a nucleic acid, a lipid, a sugar chain, an amino acid, etc. or an aggregate thereof, a virus, a cell, a metallic colloid or other non-biological molecule. When the particle used as the object to be observed is not a light-emitting particle, a particle prepared by attaching a light emitting label (a fluorescence molecule, a phosphorescence molecule, a chemiluminescence or bioluminescent molecule) with the particle to be observed in an arbitrary way is used. The sample solution is typically an aqueous solution, although not limited thereto and an organic solvent and other arbitrary liquid may be used.

The measurement of the light intensity in the inventive optical analysis may be performed in the same manner as the measurement process of the light intensity in FCS or FIDA except driving the mirror deflector 17 or stage position changing apparatus 17a to move the position of the light detection region within the sample solution (to scan in the sample solution) during the measurement. In the operation process, typically, after dispensing a sample solution into the well(s) 10 of the micro plate 9 and putting it on the stage of the microscope, when a user inputs to the computer 18 a command of a measurement start, the computer 18 executes programs memorized in a storage device (not shown) (the process of moving the position of the light detection region in the sample solution, and the process of detecting light from the light detection region during the moving of the position of the light detection region and generating time series light intensity data), and then illuminating the light detection region in the sample solution with the excitation light and measuring light intensity will be started. During this measurement, under the control of the operation process of the computer 18 according to the programs, the mirror deflector or stage position changing apparatus 17a drives the mirror 7 (galvanomirror) or the micro plate 9 on the stage of the microscope to move the position of the light detection region in the well 10, and simultaneously with this, the photodetector 16 sequentially converts the detected light into an electric signal and transmits it to the computer 18, which generates the time series light intensity data from the transmitted light signals and store it in an arbitrary manner. In this regard, the photodetector 16 is typically a super high sensitive photodetector which can detect an arrival of a single photon, and thus the time series light intensity data may be time series photon count data.

The moving speed of the position of the light detection region during the measurement of the light intensity may be a predetermined velocity set arbitrarily, for example, experimentally or in order to meet the purpose of an analysis. In a case of acquiring the information on the number density or concentration based on the number of detected light-emitting particles, the region size or volume through which the light detection region has passed is required, and therefore, the moving of the position of the light detection region is performed in a manner enabling the grasping of the moving distance. In this regard, because the interpretation of a measurement result will become easy if the elapsed time is proportional to the moving distance of the position of the light detection region, basically, it is preferable that the moving speed is constant, although not limited thereto.

Figure 3A:
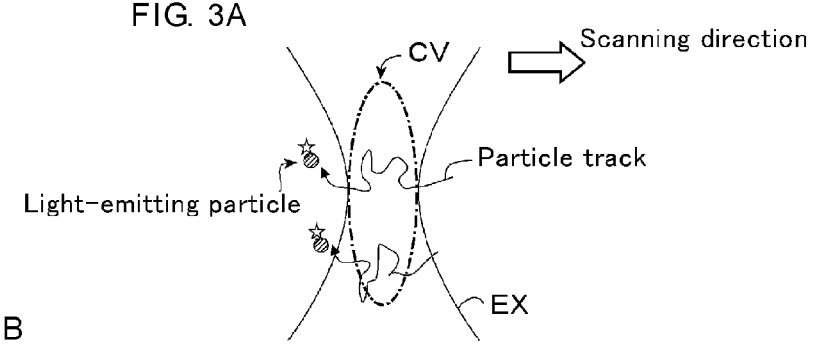
FIGS. 3A and 3B are a drawing of a model in the case that a light-emitting particle cross a light detection region owing to Brownian motion and a diagram showing the example of the variation of the photon counts (light intensity) with time in this case, respectively.
Figure 3B:
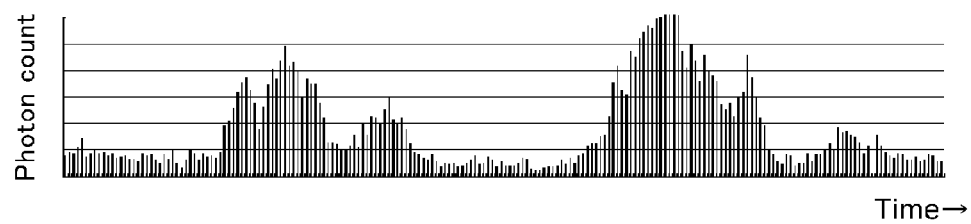

By the way, regarding the moving speed of the position of the light detection region, in order to perform quantitatively precisely individual detection of the light-emitting particles from the measured time series light intensity data or the counting of the number of the light-emitting particles, it is preferable that the moving speed is set to a value faster than the moving speed in the random motion, i.e., Brownian motion of a light-emitting particle. Since the particle to be observed in the inventive optical analysis technique is a particle dispersed or dissolved in a solution and moving at random freely, its position moves with time owing to the Brownian motion. Thus, when the moving speed of the position of the light detection region is slower than the movement of a particle owing to the Brownian motion, the particle moves at random in the region as schematically drawn in FIG. 3A, whereby the light intensity changes at random as shown in FIG. 3B (As already noted, the excitation light intensity in the light detection region is reduced from the peak at the center of the region toward its outside), so that it becomes difficult to determine a significant light intensity change corresponding to each light-emitting particle. Then, preferably, as drawn in FIG. 4A, the moving speed of the position of the light detection region is set to be faster than the average moving speed of a particle by the Brownian motion (diffusional moving velocity) so that a particle will cross the light detection region in an approximately straight line and thereby the profile of the change of the light intensity corresponding to each light-emitting particle becomes almost uniform in the time series light intensity data as illustrated in FIG. 4B (When a light-emitting particle passes through the light detection region in an approximately straight line, the profile of the light intensity change is similar to the excitation light intensity distribution) and the correspondence between each light-emitting particle and light intensity can be easily determined.

Concretely, the time $\Delta t$ required for a light-emitting particle having a diffusion coefficient D to pass through the light detection region of radius Wo (confocal volume) by Brownian motion is given from the expression of the relation of mean-square displacement:

$$(2Wo)^2 = 6D \cdot \Delta t \qquad (1)$$

as:

$$\Delta t = (2Wo)^2/6D \qquad (2),$$

and thus, the velocity of the light-emitting particle moving by Brownian motion (diffusional moving velocity) Vdif, becomes approximately $$Vdif = 2Wo/\Delta t = 3D/Wo \qquad (3)$$

Then, with reference to this, the moving speed of the position of the light detection region may be set to a value sufficiently faster than Vdif. For example, when the diffusion coefficient of a particle to be observed is expected to be about $D=2.0 \times 10^{-10}$ m$^2$/s, Vdif will be $1.0 \times 10^{-3}$ m/s, supposing Wo is about 0.62 μm, and therefore, the moving speed of the position of the light detection region may be set to its 10 times or more, e.g. 15 mm/s. In this regard, when the diffusion coefficient of a particle to be observed is unknown, an appropriate moving speed of the position of the light detection region may be determined by repeating the executions of a preliminary experiment with setting various moving speeds of the position of the light detection region in order to find the condition that the profile of a light intensity variation becomes an expected profile (typically, similar to the excitation light intensity distribution).

(2) Analysis of Light Intensity

When the time series light intensity data of a sample solution are obtained by the above-mentioned processes, an analysis of the light intensity as described below may be performed in the computer 18 through processes in accordance with programs memorized in a storage device (the process of smoothing time series light intensity data, and the process of detecting individually the light signal of each light-emitting particle in the smoothed time series light intensity data).

(i) Detection of One Light-Emitting Particle

Figure 5A:
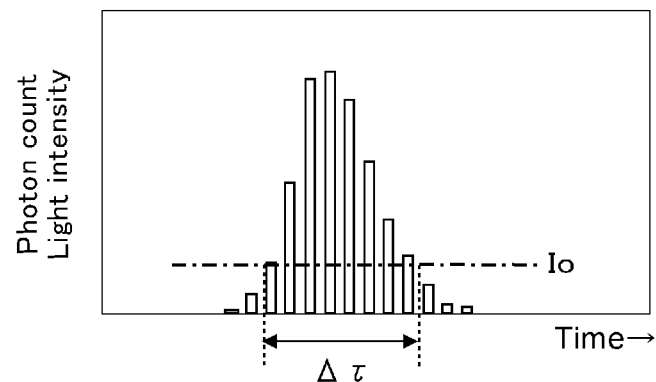

When the track of one light-emitting particle in its passing through the light detection region is approximately straight as shown in FIG. 4A, the light intensity variation corresponding to the light-emitting particle in the time series light intensity data has a profile reflecting the light intensity distribution in the light detection region (determined by the optical system) (usually approximately bell shape) as schematically drawn in FIG. 5A. Then, in one of the methods for the detection of a light-emitting particle, a threshold value Io is set for the light intensity, and when the time width Δτ for which the light intensity exceeding the threshold value continues is in a predetermined range, the profile of the light intensity may be judged to corresponds to one light-emitting particle having passed through the light detection region, and thereby one light-emitting particle is detected. The threshold value Io for the light intensity and the predetermined range for the time width Δτ are determined based on a profile expected in the intensity of the light emitted from a light-emitting particle moving relatively to the light detection region at a predetermined speed, and concrete values may be set arbitrarily or experimentally, and also may be selectively determined depending upon the characteristics of a particle to be observed.

Moreover, in another method of detection of a light-emitting particle, when the light intensity distribution in the light detection region can be assumed as Gaussian distribution:

$$I = A \cdot exp(-2t^2/a^2) \tag{4},$$

and when the intensity A and the width a, computed by fitting the expression (4) to the profile of a significant light intensity (a profile which can be clearly judged not to be a background), each are within the predetermined ranges, the profile of the light intensity is judged to correspond to one light-emitting particle having passed through the light detection region, and thereby the detection of one light-emitting particle is done (The profile with the intensity A and the width a out of the predetermined ranges may be ignored as a noise or a contaminant in the analysis.

(ii) The Counting of Light-Emitting Particles

The counting of light-emitting particles may be done by counting in an arbitrary way the number of the light-emitting particles detected by the above-mentioned method of detection of the light-emitting particle. However, for the large number of light-emitting particles, for example, the processes may be accomplished in a manner as shown below.

Figure 5B:
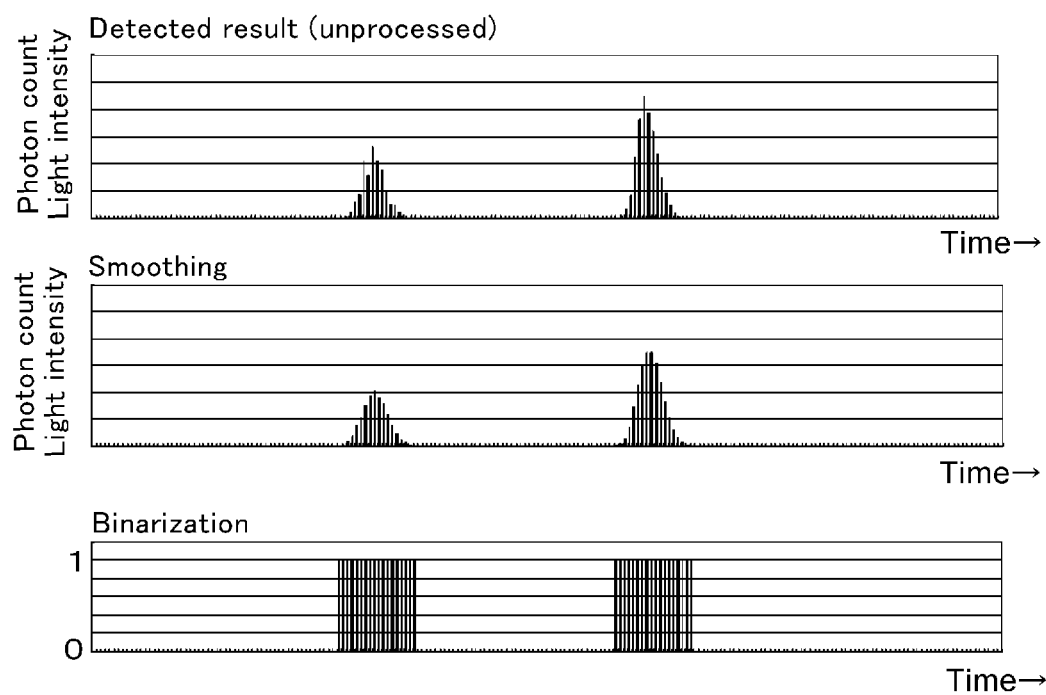

Referring to FIG. 5B, in one example of the methods of counting light-emitting particles from time series light intensity (photon count) data, first, to the detected time series photon count data (upper column), the smoothing treatment is performed (middle column). Since the emission of light from a light-emitting particle is stochastic and gaps are generated in data values in minute time, such gaps in the data value can be disregarded by the smoothing treatment. The smoothing treatment may be done for example by the moving average method. Subsequently, the binarization of the time series photon count data is carried out (lower column) by assigning 1 to the data points (time) having the intensity more than a predetermined threshold value and assigning 0 to the data points having the intensity less than the threshold value in the smoothed time series photon count data. Then, in the whole data, the number of the light-emitting particles crossing the light detection region during measurement is counted by counting the portions whose value changes 1 to 0 or 0 to 1.

Figure 6B:
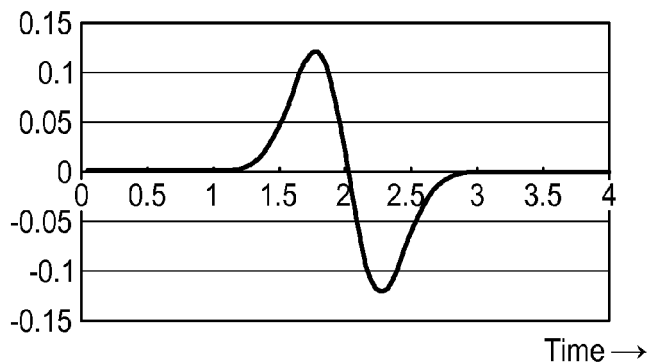

In one more other example of the methods of counting light-emitting particles from the time series light intensity (photon count) data, to the time series photon count data (FIG. 6A) to which the smoothing treatment is applied as in the case of FIG. 5B, a differentiation process is applied (FIG. 6B). In this data to which the differentiation process has been applied, because at the point of the intensity peak, its value is reducing in the direction of the time increase and the value is 0 or its quadratic differential value is 0, the number of the light-emitting particles which crossed the light detection region during measurement will be counted by counting those points.

(iii) Determination of the Number Density or Concentration of a Light-Emitting Particle When the counting of light-emitting particles has been done, the number density or concentration of the light-emitting particle can be determined using the volume of the whole region which the light detection region has passed through. However, the effective volume of the light detection region varies depending on the wave length of excitation light or detected light, the numerical aperture of lenses and the adjustment condition of the optical system, and therefore, it is difficult to compute the effective volume of the light detection region from the design parameter values. Then, in this embodiment, the light intensity measurement, the detection of light-emitting particles and the counting thereof are performed as explained above with a solution having a known light-emitting particle concentration (reference solution) under the same condition as that for the measurement of the sample solution to be tested, and then, from the detected number of light-emitting particles and the concentration of light-emitting particle in the reference solution, the volume of the whole region which the light detection region has passed through, i.e., the relation between the detected number and the concentration of the light-emitting particle, may be determined. Preferably, the light-emitting particle of a reference solution may be a light emitting label (fluorescent dye etc.) having the same wavelength characteristic as a particle to be observed. Concretely, for example, supposing the detected number of the light-emitting particles is N in a reference solution of the light-emitting particle concentration C, the volume Vt of the whole region which the light detection region has passed through is given by:

$$Vt = N/C \tag{5}.$$

Alternatively, the plurality of solutions of different concentrations of a light-emitting particle are prepared as reference solutions and the measurement is performed for each of the solutions, and then, the average value of the computed Vt is determined as the volume Vt of the whole region which the light detection region has passed through. Thus, when Vt is given, the number density c of the light-emitting particle of the sample solution, whose counting result of the light-emitting particles is n, is given by:

$$c = n/Vt \tag{6}$$

In this regard, the volume of the light detection region and the volume of the whole region which the light detection region has passed through may be given by an arbitrary method, for instance, using FCS and FIDA, instead of the above-mentioned method. Further, in the optical analysis device of this embodiment, there may be previously memorized in a storage apparatus of the computer 18 the information on the relations (expression (5)) between concentrations C and light-emitting particle numbers N of various standard light-emitting particles for assumed moving patterns of the light detection region, so that a user of the device can appropriately use the memorized information on the relation in conducting an optical analysis.

Calculation Experiment

In order to check that the counting result of light-emitting particles corresponding to the number density of a light-emitting particle in a sample solution is obtained in accordance with the principle of the inventive optical analysis technique, the following calculation experiment was conducted. FIG. 7 shows a drawing explaining about the model assumed in the calculation experiment.

Referring to the drawing, in the calculation experiment, first, there was considered a model in which a cube having the side length L is placed in an X-Y-Z coordinate such that the center of cube becomes the origin of the coordinate, and, as light-emitting particles moving at random freely within a sample solution, the positions of eight (8) particles having the diffusion coefficient D are made displaced within the cube in the random direction every time width $\Delta t=10$ μsec. The side length L of the cubic was set in accordance with the particle concentration: For example, when the particle concentration was set to 10 pM, it was set that L=11.0 μm. In this regard, in order to make eight particles always exist in the cube so that the initially set concentration will be maintained, it was designed that a particle, when moved beyond the cubic border plane (the planes of X, Y, and Z=±L/2), was made enter into the cube again from the opposite border plane (For example, when a certain particle exceeds the plane of X=L/2, the particle is made to enter into the cube from the plane of X=−L/2). Further, typically, it is expected that the light intensity obtained from an actual light-emitting particle in a sample solution changes from the peak at the center of a light detection region in the radial direction in accordance with the Gaussian distribution, and thus, in the cube, the light intensity distribution centering on the origin is set to:

$$I = A \cdot exp[-2(X^2+Y^2+Z^2)/Wo^2] \quad (7),$$

such that it was assumed that a particle located in the coordinate (X,Y,Z) in the cube emitted the light given by the expression (7). In the expression (7), A is the intensity at the center, where it was set as A=1, and Wo is a beam waist, which was set as Wo=620 nm. The sphere having a radius Wo corresponds to an effective light detection region, whose volume will be set to be approximately 1 fL. Furthermore, in the inventive optical analysis technique, the position of the light detection region is made move in a sample solution. That is, it can also be said that the space of the sample solution moves relatively to the light detection region. Thus, in the model, for modeling that the light detection region moves in the −X direction in the space (sample solution) at a moving speed V, it was designed that V·Δt was added in the X direction to the displacement in every Δt=10 μsec. of each particle in the cube. The upper column of FIG. 5B is the light intensity data obtained in the case that the particles in the cube at the particle concentration of 10 pM were displaced at 15 mm/s of the moving speed of the light detection region for 2 ms according to the above-mentioned model, and as intuitively understood from the drawing, it was confirmed that two particles passed through the light detection region and the profile of each intensity variation formed almost Gaussian distribution.

Furthermore, under an assumption that the particles in the cube at various concentrations were displaced while emitting light for an arbitrary term according to the setting of the above-mentioned model, by computing sequentially the total amount of the light intensity emitted from the space in the term, the time series light intensity data were produced, and the number of light-emitting particles was counted in the acquired time series light intensity data in accordance with the method of the counting of light-emitting particles explained above.

In the above-mentioned model, the average value and CV value (the standard deviation/average) of the count number of particles in 5 times of the repeated experiments of the counting of light-emitting particles under the condition that the particle concentration was set to 10 pM or 0.1 pM; the moving speed of the light detection region was set to 15 mm/s; and the measuring term (the term of the execution of the displacement of the particles) was 10 seconds became as follows:

| Concentration | 10 pM | 0.1 pM |
|---|---|---|
| Count number | 3668 particles | 35.6 particles |
| CV value | 1.7% | 13.3% |

As understood from this result, the count numbers of the particles almost proportional to the set particle concentrations were obtained. That is, this result indicates that, by conducting the counting of light-emitting particles, such as dye, having a certain characteristics under a condition that the light-emitting particles are excited with an excitation light of given intensity at a given moving speed of a light detection region for a given measuring term, the count number quantitatively corresponding to the concentration of the light-emitting particle can be obtained and the concentration of the light-emitting particle can be determined. Furthermore, when an experiment was conducted in the same way as above but with the moving speed of the light detection region being set to 60 mm/s, the average value and CV value (the standard deviation/average) of the count number of particles became as follows:

| Concentration | 10 pM | 0.1 pM |
|---|---|---|
| Count number | 11499 particles | 126 particles |
| CV value | 1.1% | 9.4% |

According to this result, it is shown that, if the moving speed of the light detection region is increased, the CV value decreases so that it is possible to reduce the dispersion in counting light-emitting particles. Furthermore, in a similar experiment conducted with the particle concentration of 1 fM and the moving speed of the light detection region 100 mm/s, the average value and CV value (the standard deviation/average) of the count number of particles became 11.6 particles and 7.7%, respectively. According to this result it is suggested that, in this invention, counting light-emitting particles can be performed even at a concentration of a particle to be observed significantly lower than concentrations usually used in FCS and FIDA.

Thus, according to the above-mentioned inventive optical analysis technique, by moving, in a sample solution, the position of a micro region, i.e. a light detection region, namely scanning the inside of the sample solution and detecting individually a light-emitting particle crossing the light detection region or conducting the counting of the light-emitting particles, where no statistical procedures, such as calculation of fluorescence intensity fluctuation, performed in FCS, FIDA, etc., are included, it becomes possible to detect a condition or a characteristic of a particle to be observed in a sample solution whose the concentration or number density of the particle to be observed is lower than the level used in FCS, FIDA, etc.

In this regard, since the inventive optical analysis technique basically uses the same optical system as FCS, FIDA, etc. it may be performed together with FCS, FIDA, etc. For example, in a case of detecting an interaction, etc. between two or more kinds of substances in a solution containing of these, when the concentration difference between substances is large, for example when the concentration of one substance is nM order and that of the other substance is pM order, there can be conducted a manner that measurement and analysis are conducted by FCS or FIDA for the substance of the higher concentration while measurement and analysis are conducted by the inventive optical analysis technique for the substance of the lower concentration. In such a case, as illustrated in FIG. 1A, it is advantageous to prepare two or more photodetectors.

In order to verify the validity of the present invention explained above, the experiments described below were conducted. In this regard, it should be understood that the following embodiments illustrate the validity of the present invention only, not intended to limit the scope of the present invention.

Embodiment 1

The concentration range of a light-emitting particle in a sample solution which can be measured by the present invention was verified using a fluorescent dye, ATTO633 (sigma Aldrich Cat. No. 18620) as the light-emitting particle. In this regard, as a control experiment, the range of the light-emitting particle concentration measurable according to a fluorescence intensity measured with a plate reader was also measured.

For the sample solutions, phosphate buffers (including 0.05% Tween20) including ATTO633 at its concentration of 0 fM (with no dye), 10 fM, 100 fM, 1 pM, 10 pM, 100 pM, and 1 nM were prepared, respectively. In this regard, solutions containing ATTO633 at 10 nM and 100 nM were also prepared for control experiments.

In the measurement in accordance with the inventive optical analysis technique, a single molecule fluorescence measuring apparatus MF-20 (Olympus Corporation), equipped with the optical system of a confocal fluorescence microscope and a photon counting system was used as the optical analysis device, and time series light intensity data were acquired for the above-mentioned respective sample solutions in accordance with the manner explained in the above-mentioned "(1) Measurement of the light intensity of a sample solution". For the objective, a water immersion objective (40×, NA=1.15, WD=0.26) was used. In this connection, for the photodetector 16, a super high sensitive photodetector capable of detecting an arrival of a single photon was used, and thereby the light detection was the photon counting performed sequentially for a predetermined term in a manner that the number of photons arriving at the photodetector in every predetermined unit time (BIN TIME) was measured. Accordingly, the time series light intensity data is time series photon count data. Further, a 633 nm laser light was used for excitation light, and the detected light wavelength was set from 660 to 710 nm using a band pass filter. Measurement for 2 seconds was performed 3 times, where the moving speed of the position of the light detection region in the sample solution was set to 15 mm/second and BIN TIME was set to 10 μsec. An example of the time series photon count data obtained by a measurement for 2 seconds is shown in FIG. 8A.

After the above-mentioned light intensity measurement, light signals detected in the acquired time series photon count data for each sample solution were counted in accordance with the following procedures:

(a) Smoothing treatment of time series photon count data—By the moving average method, the smoothing of time series photon count data was performed. The data points averaged at once were nine (9) points, and the moving average treatment was repeated 5 times. FIG. 8B shows the result of smoothing the data in FIG. 8A.

(b) Detection of pulse form signal existing regions in time series photon count data—The starting point and end point of each pulse form signal in the time series photon count data after the smoothing treatment obtained by treatment of (a) were determined, and the regions where a pulse form signal exists were defined. Concretely, first, throughout the time series photon count data after the smoothing treatment, the first differential value with time was calculated to prepare the differential value data of the time series photon count data. Then, with reference to the value on the differential value data of the time series photon count data, as schematically illustrated in FIG. 8D, the point at which the change of the differential value of a pulse form signal becomes large was chosen as the start point of the pulse form signal, while the point at which the change of the differential value of a pulse form signal becomes small was chosen as the end point of the pulse form signal, and accordingly, the region between the start point and end point was defined as a pulse form signal existing region. The defining of a pulse form signal existing region was performed throughout the time series photon count data.

(c) Fitting of a bell shape function—As a bell shape function, the gauss function of the expression (4) was fitted to each of the pulse form signal existing region defined in the process (b). The fitting was performed by the least square method, where the peak intensity A, peak width (full width at the half maximum) a and correlation coefficient (in the gauss function) were determined. FIG. 8C shows the functions fitted to the data of FIG. 8B.

(d) The counting of light-emitting particles—Referring to the peak intensities, peak widths and correlation coefficients of the fitted functions, only the pulse form signals satisfying the following conditions:

20 μsec.<peak width<400 μsec.

Peak intensity>1(photon/10 μsec.)

Correlation coefficient>0.95     (A)

were judged as a light signal corresponding to a light-emitting particle, while pulse form signals which did not satisfy the above-mentioned conditions were disregarded as noise, and the number of the signals judged as a light signal corresponding to a light-emitting particle was counted as a "pulse number." FIG. 9 shows an example of a signal judged as a light signal of a light-emitting particle and an example of a signal judged as noise.

In the control experiment, fluorescence intensity was measured for each of the above-mentioned sample solution using a plate reader SH-8000lab (Corona). The excitation light wave length was set to 633 nm; the detected light wavelength, to 657 nm; and both the band widths of the excitation and detection sides, to 12 nm. In measuring the fluorescence intensity, 3 times of measurement where 50 times of excitation light flash were applied were performed, and their average was used as the final fluorescence intensity value.

FIGS. 10A and 10B each show the measurement results (pulse number) by the above-mentioned inventive optical analysis technique and the measurement results (fluorescent intensity) in the control experiment, detected in the sample solutions of the respective concentrations (Each value is the average of three measurements, respectively). Referring to FIG. 10A first, the pulse number measured by the present invention (the number of the signals counted as the light signal of the light-emitting particle) increased almost in proportion to the light-emitting particle concentration in the range on and above 100 fM of light-emitting particle concentration. According to this result, it has been found that the inventive optical analysis technique enables detecting a light emitting particle one by one, and that, by counting individual light-emitting particles according to the inventive optical analysis technique, the light-emitting particle concentration can be determined quantitatively.

Further, while no significant difference between the fluorescence intensity in the case of the light-emitting particle concentration of 0 M and the fluorescence intensity in the case of the light-emitting particle concentration of 100 pM can be recognized in the control experiment of FIG. 10B, the significant difference was seen between the pulse number in the case of the light-emitting particle concentration of 0 M and the pulse number in the case of the light-emitting particle concentration of 100 fM in the inventive optical analysis technique of FIG. 10A. The reason of these results is considered as follows: On the fluorescence intensity measured with the plate reader, the light signals owing to noises or contaminants were superposed and accordingly the S/N ratio got worse in the low concentration range where the contribution of noises or contaminants to the fluorescence intensity is relatively large. On the other hand, in the case of the present invention, it was judged whether or not each pulse form signal in time series light signal data corresponded to a light-emitting particle, and signals judged as noises or contaminants were disregarded (see FIG. 9), and therefore even in the low concentration region where the contribution of noises or contaminants to the fluorescence intensity is large relatively, the S/N ratio was maintained to be comparatively good. Actually, regarding the total photon number in time series photon count data measured in each sample solution in the measurement for 2 seconds according to the inventive optical analysis technique, as shown in FIG. 10C, in the range of light-emitting particle concentration less than 100 pM, no significant difference from the case of light-emitting particle concentration of 0 M was observed. Namely, it has been shown that, according to the present invention, by detecting a light signal of a light-emitting particle from time series photon count data and counting its number, instead of counting the photon number in time series photon count data, the sensitivity in the detection of concentration is improved significantly (In the case of the present embodiment, two order lower concentration was measurable).

Furthermore, regarding the above-mentioned signal processing of time series photon count data, the effect of the smoothing treatment to time series photon count data was verified. FIGS. 11A and 11B each are graph charts showing the numbers of the light signals with respect to each of the sample solutions containing the light-emitting particle at 100 fM, 1 pM and 10 pM, the light signals being detected by performing the above-mentioned processes (b)-(d) to time series photon count data to which the smoothing treatment was not applied and time series photon count data to which the smoothing treatment was applied and satisfying the conditions (A). As shown clearly in the drawings, the number of the light signals detected in the time series photon count data to which the smoothing treatment is applied and satisfying the conditions (A), i.e., the detected number of the light-emitting particle was decreased together with the light-emitting particle concentration as low as 100 fM, as already described, while the number of the light signals detected in the time series photon count data to which no smoothing treatment was applied and satisfying the conditions (A) did not correlate with the light-emitting particle concentration not higher than 10 pM. This suggests that a light signal corresponding to a light-emitting particle becomes detectable and a light-emitting particle concentration can be determined more precisely by applying the smoothing treatment to raw time series photon count data, in accordance with the inventive technique.

Thus, it has been shown that, according to the inventive optical analysis technique, the number density or concentration of a light-emitting particle can be determined to the concentration range lower than the limit of the number density or concentration measurable by conventional methods using fluorescence intensity. Further, while the lower limit of particle concentration measurable in optical analysis techniques, such as FCS, FIDA, and PCH, including statistical procedures, e.g. calculation of fluorescence intensity fluctuation was about 1 nM, the lower limit of the particle concentration measurable in the present embodiment was ~100 fM, and accordingly, it has been also shown that, according to the present invention, the measurement is possible for a particle in the range of a concentration significantly lower than the case of the optical analysis techniques such as FCS, FIDA and PCH. In the present application, "computer readable storage device" does not cover transitory propagating signals per se.

We claim:

1. An optical analysis device which detects light from a light-emitting particle dispersed and moving at random in a sample solution by using an optical system of a confocal microscope or a multiphoton microscope, wherein the device comprises:
    a light detection region moving mechanism moving a position of a light detection region of the optical system in the sample solution;
    a light detector detecting light from the light detection region; and
    a signal processor generating time series light intensity data of the light from the light detection region detected with the light detector during moving the position of the light detection region in the sample solution, smoothing the time series light intensity data and then detecting individually a light signal from each light-emitting particle in the smoothed time series light intensity data.

2. The device of claim 1, wherein the signal processor counts the number of the individually detected light signal(s) from the light-emitting particle(s) to count the number of the light-emitting particle(s) detected during moving the position of the light detection region.

3. The device of claim 1, wherein the light detector detects the light from the light detection region by photon counting, and the time series light intensity data is time series photon count data.

4. The device of claim 1, wherein the light detection region moving mechanism moves the position of the light detection region at a predetermined speed.

5. The device of claim 1, wherein the light detection region moving mechanism moves the position of the light detection region at a velocity faster than a diffusional moving velocity of the light-emitting particle.

6. The device of claim 1, wherein the signal processor detects the entering of one light-emitting particle into the light detection region based upon a shape of a light signal in the smoothed time series light intensity data.

7. The device of claim 1, wherein the signal processor detects the entering of one light-emitting particle into the light detection region when a light signal having an intensity larger than a predetermined threshold value is detected in the smoothed time series light intensity data.

8. The device of claim 1, wherein the signal processor determines a number density or a concentration of the light-emitting particle in the sample solution based on the number of the detected light-emitting particle(s).

9. An optical analysis method of detecting light from a light-emitting particle dispersed and moving at random in a sample solution by using an optical system of a confocal microscope or a multiphoton microscope, said method comprising steps of:
moving a position of a light detection region of the optical system in the sample solution;
detecting light from the light detection region while moving the position of the light detection region in the sample solution and generating time series light intensity data;
smoothing the time series light intensity data; and
detecting individually a light signal from each light-emitting particle in the smoothed time series light intensity data.

10. The method of claim 9, further comprising a step of: counting the number of the individually detected light signal(s) from the light-emitting particle(s) to count the number of the light-emitting particle(s) detected during moving the position of the light detection region.

11. The method of claim 9, wherein, in the step of detecting light from the light detection region and generating time series light intensity data, the light from the light detection region is detected by photon counting, and the time series light intensity data is time series photon count data.

12. The method of claim 9, wherein, in the step of moving the position of the light detection region, the position of the light detection region is moved at a predetermined speed.

13. The method of claim 9, wherein, in the step of moving the position of the light detection region, the position of the light detection region is moved at a velocity faster than a diffusional moving velocity of the light-emitting particle.

14. The method of claim 9, wherein, in the step of detecting individually the light signal from each light-emitting particle, the entering of one light-emitting particle into the light detection region is detected based upon a shape of the light signal in the smoothed time series light intensity data.

15. The method of claim 9, wherein the entering of one light-emitting particle into the light detection region is detected when a light signal having an intensity larger than a predetermined threshold value is detected in the smoothed time series light intensity data.

16. The method of claim 9, further comprising a step of determining a number density or a concentration of the light-emitting particle in the sample solution based on the number of the detected light-emitting particle(s).

17. A computer readable storage device having a computer program product including programmed instructions for optical analysis for detecting light from a light-emitting particle dispersed and moving at random in a sample solution by using an optical system of a confocal microscope or a multiphoton microscope, said programmed instructions causing a computer to perform steps of:
moving a position of a light detection region of the optical system in the sample solution;
detecting light from the light detection region while moving the position of the light detection region in the sample solution and generating time series light intensity data;
smoothing the time series light intensity data; and
detecting individually a light signal from each light-emitting particle in the smoothed time series light intensity data.

18. The computer readable storage device of claim 17, further comprising a step of: counting the number of the individually detected light signal(s) from the light-emitting particle(s) to count the number of the light-emitting particle(s) detected during moving the position of the light detection region.

19. The computer readable storage device of claim 17, wherein, in the step of detecting light from the light detection region and generating time series light intensity data, the light from the light detection region is detected by photon counting, and the time series light intensity data is time series photon count data.

20. The computer readable storage device of claim 17, wherein, in the step of moving a position of a light detection region of the optical system, the position of the light detection region is moved at a predetermined speed.

21. The computer readable storage device of claim 17, wherein, in the step of moving a position of a light detection region of the optical system, the position of the light detection region is moved at a velocity faster than a diffusional moving velocity of the light-emitting particle.

22. The computer readable storage device of claim 17, wherein, in the step of detecting individually the light signal from each light-emitting particle, the entering of one light-emitting particle into the light detection region is detected based upon a shape of the light signal in the smoothed time series light intensity data.

23. The computer readable storage device of claim 17, wherein, in the step of detecting individually the light signal from each light-emitting particle, the entering of one light-emitting particle into the light detection region is detected when a light signal having an intensity larger than a predetermined threshold value is detected.

24. The computer readable storage device of claim 17, further comprising a step of determining a number density or a concentration of the light-emitting particle in the sample solution based on the number of the detected light-emitting particle(s).

* * * * *